US006504085B1

(12) United States Patent
Howard

(10) Patent No.: US 6,504,085 B1
(45) Date of Patent: Jan. 7, 2003

(54) METHODS OF COMMERCIAL PRODUCTION AND EXTRACTION OF PROTEIN FROM SEED

(75) Inventor: John A. Howard, College Station, TX (US)

(73) Assignee: ProdiGene, Inc., College Station, TX (US)

(*) Notice: Subject to any disclaimer, the term of this patent is extended or adjusted under 35 U.S.C. 154(b) by 0 days.

(21) Appl. No.: 09/403,686

(22) PCT Filed: Mar. 20, 1997

(86) PCT No.: PCT/US97/04526

§ 371 (c)(1),
(2), (4) Date: Sep. 7, 1999

(87) PCT Pub. No.: WO98/39461

PCT Pub. Date: Sep. 11, 1998

Related U.S. Application Data

(60) Provisional application No. 60/040,119, filed on Mar. 7, 1997.

(51) Int. Cl.$^7$ .............................. A01H 5/00; A01H 5/10; C12N 5/04; C12N 15/82; C12P 21/00
(52) U.S. Cl. ...................... 800/288; 800/287; 800/278; 800/298; 800/320; 435/468; 435/419; 435/69.1; 435/183; 435/185; 530/412; 530/427
(58) Field of Search ................................ 435/69.1, 183, 435/185, 419, 468; 800/278, 287, 288, 298

(56) References Cited

U.S. PATENT DOCUMENTS

| | | | |
|---|---|---|---|
| 5,420,034 A | | 5/1995 | USX |
| 5,767,379 A | * | 6/1998 | Baszczynski et al. ........ 800/205 |
| 5,804,697 A | * | 9/1998 | Bruce et al. ................. 800/205 |
| 5,889,189 A | * | 3/1999 | Rodriguez et al. ........... 800/205 |
| 6,252,134 B1 | * | 6/2001 | Vasil et al. .................. 800/278 |

FOREIGN PATENT DOCUMENTS

| | | |
|---|---|---|
| EP | 0255378 A | 2/1988 |
| WO | WO9400992 A | 1/1994 |
| WO | WO9640949 A | 12/1996 |
| WO | WO9710347 A | 3/1997 |
| WO | WO9717453 A | 5/1997 |

OTHER PUBLICATIONS

Vandekerckhove, J. et al., "Enkephalins Produced in Transgenic Plants Using Modified 2S Seed Storage Proteins." 1989, Bio/Technology, vol. 7, pp. 929–932.*

Roberts, B. E. and Paterson, B. M. "Efficient Translation of Tobacco Mosaic Virus RNA and Rabbitt Globin 9S RNA in a Cell–Free System from Commerical Wheat Germ." 1973, Proc. Nat. Acad. Sci. USA, vol. 70, pp. 2330–2334.*

Kusnadi, A. R. et al., "Production and Purification of Two Recombinant Proteins from Transgenic Corn."1998, Biotechnol. Prog., vol. 14, pp. 149–155.*

Kusnadi, A.R. et al., "Processing of Transgenic Corn Seed and Its Effect on the Effect on the Recovery of Recombinant B–Glucuronidase." 1998, Biotechnol. Bioengineering, vol. 60, pp. 44–52.*

Fiedler, U. and Conrad, U. "High–Level Production and Long–Term Storage of Engineered Antibodies in Transgenic Tobacco Seeds." 1995, Bio/Technology, Vol. 13, pp. 1090–1093.*

Baumlein, H. et al., "Upstream sequences regulating legumin gene expression in heterologous transgenic plants." 1991, Mol Gen Genet, vol. 225, pp. 121–128.*

Altenbach, S.B. et al., "Accumulation of a Brazil nut albumin in seeds of transgenic canola results in enhanced levels seed protein methionine." 1992, Plant Molecular Biology, vol. 18,pp. 235–245.*

Hood, E.E., et al.: "Commerical Production of Avidin from Transgenic Maize", In Vitro,, vol. 32, No. 3, Jun. 27, 1996, pp. Pt. 2–67A.

Gallusci, P. et al.: "Differences in Cell Type–Specific Expression of the Gene Opaque 2 in Maize and Transgenic Tobacco", Molecular and General Genetics vol. 244, 1994, pp. 391–400.

Goldberg, R.B. et al.: "Regulation of Gene Expression During Plant Embryogenesis", Cell, vol. 56, Jan. 27, 1989, pp. 149–160.

Skokut, T.A., et al.: "Expression of a Coriander Palmitoyl–ACP Delta 4 Desaturase in Transgenic Maize", Supplement To Plant Physiology vol. 111, No. 2, 1996, p. 167.

Cornejo, M–J., et al.: "Activity of a Maize Ubiquitin Promoter in Trnasgenic Rice", Plant Molecular vol. 23, 1993, pp. 567–581.

Hood, E.E., et al., "Commerical Production of Gus from Transgenic Maize Seed", In Vitro vol. 33, NO. 3, Jun. 14, 1997, pp. Pt 2–55A.

Bruce, et al. "Maize Uiquitin 1::GUS Expression in Transgenic Maize" In Vitro VO.32 No.3, Jun. 22–27, p. 73A.

Holtorf et al. "Comparison of Different Constitutive and Inducible Promoters For the Overexpression of Transgenes in *Arabidopsis thaliana*" Plant Mol. Biol. 29:637–646, 1995.

Hood et al. "Commerical Production of Avidin From Transgenic Maize: Characterization of Transformant, Production, Processing, Extraction and Purification" Mol. Breeding 3:219–307 (1997).

(List continued on next page.)

*Primary Examiner*—David T. Fox
*Assistant Examiner*—Anne Kubelik
(74) *Attorney, Agent, or Firm*—Patricia Sweeney

(57) ABSTRACT

A method for extraction of heterologous protein from plant seed comprises extracting the germ portion of the seed and extracting and purifying the protein from the germ. Enhanced expression in the germ is provided, and allows for improved efficiency in production, and cost savings. Directing expression to the germ portion further increases expression levels of the protein. The ubiquitin promoter preferentially directs expression to the germ portion of plant seed.

5 Claims, 13 Drawing Sheets

OTHER PUBLICATIONS

Kusnadi et al. "Recovery of Recombinant β–Glucuronidase from Transgenic Corn" The Proceedings of the $26^{26}$ Annual Biochemical Engineering Erickson, L.E., Ed.; Kansas State University, Manhattan Kansas pp. 143–152 (1997).

Skotut T. et al. *Plant Physiology*, supplement (1996) vol. 111, No. 2, p. 167.

Holtorf et al., "Comparison of different constitutive and inducible promoters for the over expression of transgenes in *Arabadopsis thaliana*" *Plant Mol. Biol.* 29: 637–646 (1995).

Bruce et al., "Maize Ubiquitin 1:GUS expression in Trangenic maize" In Vitro (1996) 32 pt. 2 p. 73A.

Kusnadi, et al. "Recovery of Recombinant β–Glucuronidase from Transgenic Corn" THE PROCEEDINGS OF THE $26^{th}$ ANNUAL BIOCHEMICAL ENGINEERING Erickson, L.E. Ed.: Kansas State University, Manhattan Kansas pp. 143–152 (1997) and orally presented Sep. 21, 1996.

* cited by examiner

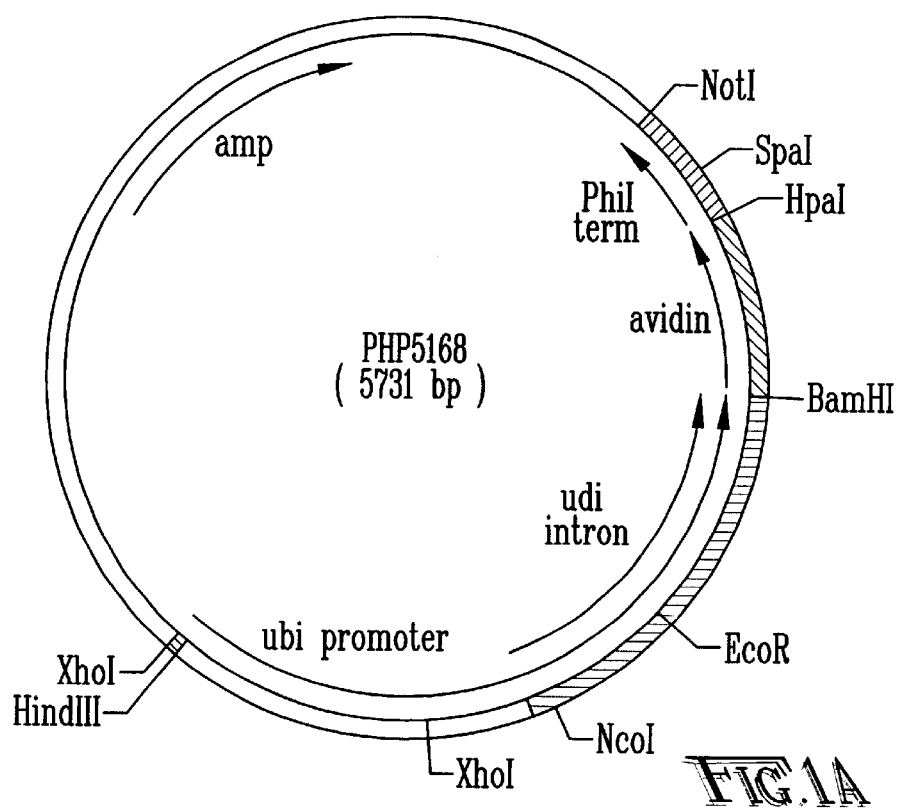
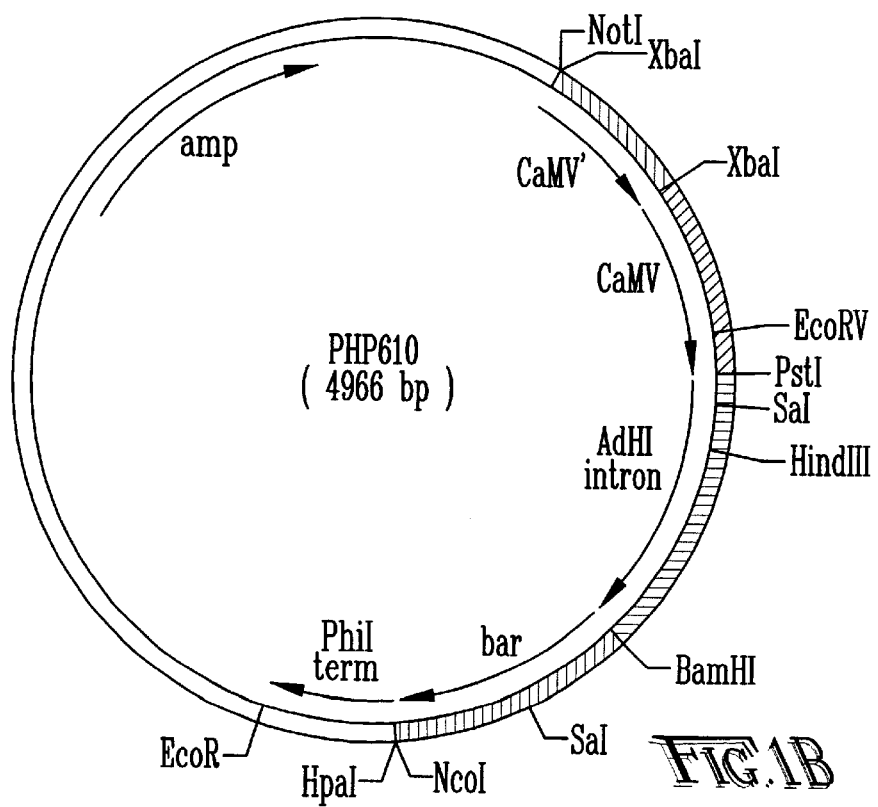

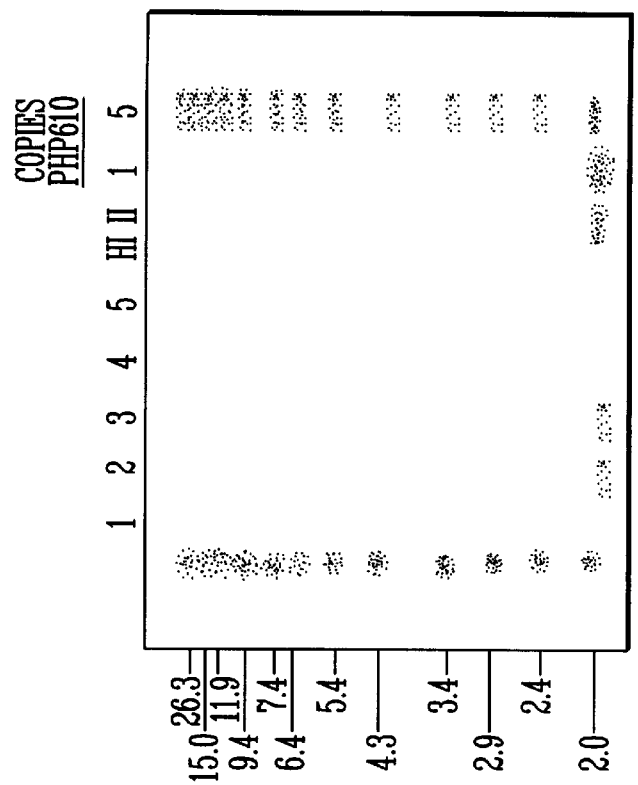
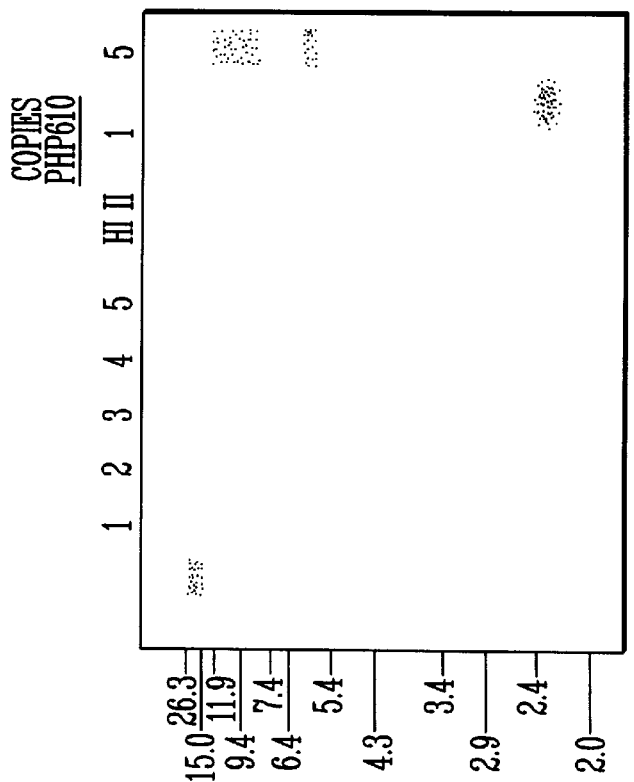

METHODS OF COMMERCIAL PRODUCTION AND EXTRACTION OF PROTEIN FROM SEED

This application is a continuation and section 371 filing of and is a 35 USC§371 filing of previously filed and copending application PCT/US97/04526, filed Mar. 20, 1997, which claims priority to previously filed and copending provisional application 60/040,119 filed Mar. 7, 1997

BACKGROUND OF THE INVENTION

For decades, many proteins useful to humans or animals have been isolated from plants. With the advent of genetic engineering technology, a plant could be modified to produce human, animal, viral, bacterial, or fungal proteins. Transgenic plants offer the potential to be one of the most economical systems for large-scale production of proteins for industrial, pharmaceutical, veterinary and agricultural use. Advantages of plant systems include the low cost of growing a large biomass, easy scale-up (increase of planted acreage), natural storage organs (tubers, seeds), and established practices for efficient harvesting, transporting, storing, and processing of the plant. Recombinant proteins can be targeted to seeds allowing stable storage of the recombinant proteins for extended periods. Plants offer advantages over other production systems since some proteins may be used without extensive purification, because for many applications, plant material is used directly as a food source or feed stock.

Examples abound for expression of foreign genes in plants [1, 2][1] In general, the expression of these foreign genes has been aimed at benefiting the consumer through plant improvement by: a) expressing antifungal compounds or growth factors; b) improving agronomic traits such as fruit ripening or nutritional contents or c) inducing sterility in the context of creating hybrid plants. It is also feasible to express in plants heterologous genes that encode high value products, a technology currently being explored by several plant biotechnology companies and university laboratories. In many cases, expression in plants could be the system of choice because of such inherent advantages as cost relative to that of animal tissue culture, and the concern that prokaryotic or yeast expression systems may not be capable of correct glycosylation and other post-translational processing steps required for proper function of the expressed protein [3]. Thus, there is a need to improve such systems for increased efficiency of expression of the protein and to lower production costs.

[1] References are listed at the end of the Detail Description of the Specific Embodiments.

Among representative efforts to achieve such goals is the Goodman et al patent assigned to Calgene, U.S. Pat. No. 5,550,038, which discloses constructs for expression of physiologically active mammalian proteins in plant cells. The isolation and purification procedure for the mammalian peptides disclosed there is to preparation from frozen tobacco tissue obtained from tissue culture which is ground in liquid nitrogen, centrifuged, washed with ethylene glycol and dialyzed overnight in dialysis buffer to obtain γ-IFN.

Vanderkerckhove et al, assigned to Plant Genetic Systems N.V, at U.S. Pat. No. 5,487,991, discloses a method for producing polypeptides by cultivating a plant whose genome contains recombinant DNA. Recovery of transgenic proteins is accomplished by harvesting seeds from cultivated plants, cleaving out the peptide of interest and recovering the peptide of interest in a purified form. The recovery of the active polypeptides involves homogenizing the entire seed in dry ice and extraction with hexane, extraction with high salt buffer and dialysis against distilled water and precipitating the contaminating globulins. Further purification is accomplished by gel-filtration chromatography, and finally ion-exchange chromatography.

The extraction process shown at PCT W092/010402 by Willmitzer et al and assigned to Novo Nordisk provides for homogenizing plant tissue and use of extraction buffer, filtration and centrifugation.

In PCT W095/14099 by Rodriguez et al, assigned to the University of California, methods for production and secretion of heterologous proteins in plants are discussed wherein malting monocot plant seeds is disclosed to stimulate heterologus protein production in cereal seeds, causing conversion of the endosperm to maltose and germination of the seeds. The chimeric gene includes a transcriptional regulatory region inducible during seed germination, a DNA sequence encoding a protein of interest and further contains a signal sequence linked to the transcriptional regulatory region effective to facilitate secretion of the protein across the aleurone or scutellar epithelium layer into the endosperm. In one embodiment, the embryos and endosperm may be separately steeped in 55° F. water for 48 hours followed by four day germination in bins or drums with inducement of a promoter or addition of plant hormones. This is because expression in the embryo was poor unless different conditions were used to cause induction of the protein in the embryo versus the endosperm. The embryo and endosperm portions are then mixed and mashed.

Factors that can be manipulated to control levels of expression are the presence of transcriptional modification factors such as introns, polyadenylation signals and transcription termination sites. Intron sequences within the gene of interest also may increase its expression level by stabilizing the transcript and allowing its effective translation. Many plant genes contain intron sequences exhibiting this positive impact on expression [4] including for example some of the plant ubiquitin genes [5,6] and the Adh2 gene [4]. At the translational level, factors to consider that affect expression level of foreign genes are the ribosomal binding site and the codon bias of the gene [7, and references therein]. High level expression of a gene product which accumulates in the cytoplasm may result in toxicity to the plant cell. Therefore, sequestering the protein into a compartment (organelle) or transporting it to the extracellular matrix may allow higher expression levels. Efforts are being made to understand plant protein targeting [8,9] and proteins can be effectively targeted to the mitochondrian, the chloroplast, the vacuole, peroxisomes or the cell wall. The specific choice of where to target will depend on the nature of the protein of interest and the specific need. Insertion of a construct at different loci within the genome has been observed to cause variation in the level of gene expression in plants. The effect is believed to be due at least in part to the position of the gene on the chromosome, producing individual isolates with different expression levels[10].

One of the critical factors in expression of protein in plants is the choice of transcriptional promoters used. Recently, the range of available plant compatible promoters has increased to include tissue-specific and inducible promoters. Some of the better documented constitutive promoters include the CaMV 35s promoter and its tandem arrangement, as described in European patent application number 0 342 926, and the ubiquitin promoter, as disclosed in Quail et al, assigned to Mycogen Plant Science, Inc. U.S. Pat. No. 5,510,474.

The invention here improves on what has been known through the determination that the germ can be separated from the endosperm, not for enriching the endosperm fractions, but to be used separately for recovery of protein and high activity obtained. This provides for considerable cost savings, as the separated endosperm and other part of the seed can be sold for food and feed, and the much smaller germ material as opposed to the entire seed, is processed, producing more protein per material processed.

Further, expression of protein can be directed to the germ, further enhancing protein recovery. A surprising finding is that the ubiquitin promoter, believed to have been constitutively expressed, greatly increases expression of protein in the germ.

Thus it is an object of the invention to decrease cost in production of commercial protein through using seed expressing the protein.

An object of the invention is to use seed for production of commercial protein more efficiently.

It is another object of the invention to use the germ portion of the seed for production of commercial protein while retaining high activity of the recombinant protein.

Another object of the invention is to increase expression of heterologous protein in seed of a plant.

A still further object of the invention is to direct expression of heterologous protein in a seed to the germ or embryo portion of the seed.

Yet another object of the invention is to use the ubiquitin promoter to direct expression of heterologous protein to the germ portion of plant seed.

The foregoing objectives and others will become apparent in the description below. All references cited are incorporated herein by reference.

SUMMARY OF THE INVENTION

The germ of a plant seed is separated from the rest of the seed into which a heterologous gene expressing a protein has been introduced. High activity of the protein is maintained by the germ, increasing protein recovery, lowering production cost and providing more efficient the germ, increasing protein recovery, lowering production cost and providing more efficient utilization of the plant seed. Promoters directed to the germ further enhance recovery. The ubiquitin promoter gives very high expression preferentially in the embryo.

BRIEF DESCRIPTION OF THE DRAWINGS

FIG. 1: Restriction endonuclease maps of plasmids used for maize transformation to generate the avidin-1 line. A. PHP5168 is composed of the maize ubiquitin promoter and nontranslated first exon with intron, a barley alpha amylase signal sequence, a gene encoding chicken avidin and the PinII terminator cloned into a Bluescript SK+ plasmid backbone. B. PHP610 is composed of the tandem CaMV promoter followed by the AdH1 intron from maize, the bar gene and the PinII terminator cloned into Bluescript SK+. amp=resistance to ampicillin.

FIG. 2: DNA blot hybridization analysis of avidin-1 plants with the avidin gene specific probe (A) or the bar gene specific probe (B). A. DNA was extracted from five plants (T1 generation). The DNA was digested with SphI and SpeI to generate fragments within the plant transcription unit. Three plants were positive in this hybridization experiment. Lanes 1–5 represent individual plants. Copies 1 and 5 refer to plasmid DNA loaded in one and five copy number reconstructions. The intensity and number of bands indicate the number of copies of the gene in the transgenic plant. B. DNA from the same preps as in A was digested with EcoRI and XbaI to generate fragments within the plant transcription unit. Information from this blot indicates the number of copies of the gene in the transgenic plant. Lanes are the same as in A.

DESCRIPTION OF THE SPECIFIC EMBODIMENTS

Figure 3A:
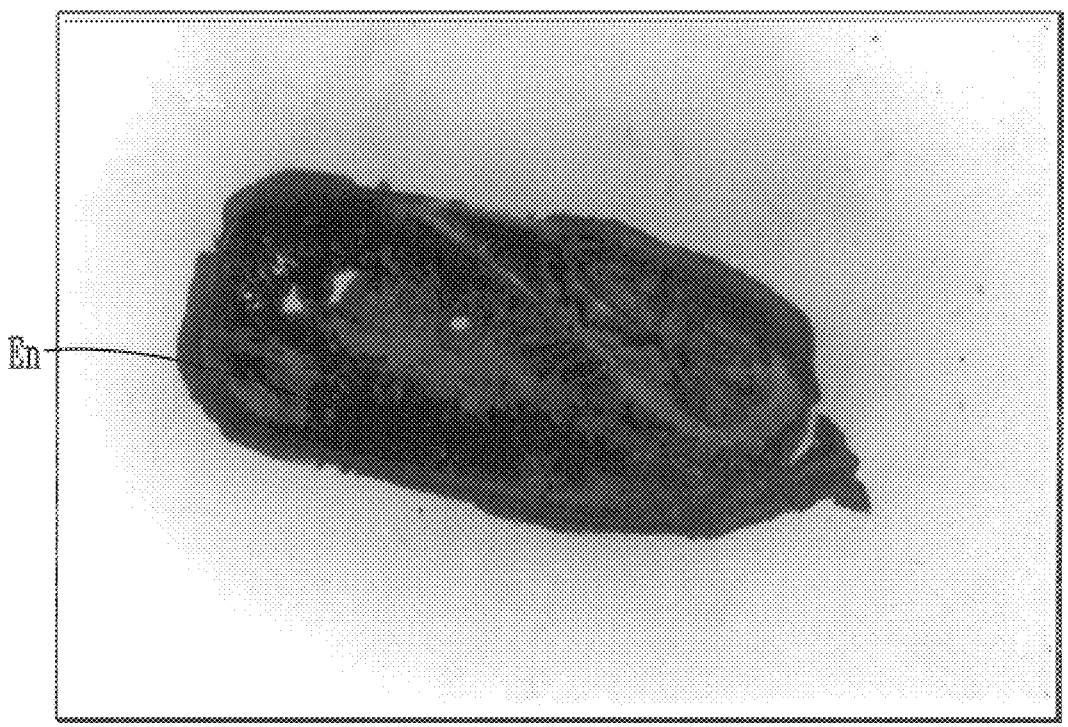
FIG. 3: Tissue prints of near mature kernels from an avidin-positive plant (A–C) or an avidin-negative plant (D). A. Tissue print stained for total protein with India Ink. B, C. Tissue prints incubated with the anti-avidin antibody (ICN, 1:1000 dilution) and an alkaline phosphatase conjugated secondary antibody (Sigma Chemical Co., 1:1000 dilution). Note high concentration of avidin protein in the embryo (E). D. Avidin-negative kernel tissue print incubated as in B and C. Ax, embryonic axis; Sc, scutellum; En, endosperm. Bars represent 1 mm.

The inventors have determined that when heterologous genes are introduced into a plant for expression of protein of interest, the germ portion of the seed may be separated from the remaining portions of the seed, with high levels of protein obtained. Surprising high activity of the recombinant protein is maintained. For example, as discussed below, in transgeneic maize seeds, 80% of the total kernel weight is endosperm, yet it contained only 22% of the avidin activity found in whole kernels. The embryo contained at least 55% of the avidin protein found in whole dry seed. In another example, rGUS concentration was six to ten times greater in the germ extract than in the kernel extract. Since the germ represents 10% of the corn seed, only small amounts of material must be used in downstream extraction and processing of the protein and in that 10% there is considerably more enrichment of the protein than in the seed as a whole. Increased efficiency in processing is thus achieved. Further, the 90% of the seed remaining can be used as a normal corn product for feed or food, thus resulting in additional revenues in the commercial protein production process.

Direction of expression of the protein to the germ is preferred according to the invention. It has been further determined by the inventors that the ubiquitin promoter directs expression preferentially to the germ of the seed. The example below demonstrates the ubiquitin promoter induced 10 to 20 fold higher levels of expression of the desired protein in seed as compared with other seed specific promoters.

In one embodiment of the invention, a gene expressing the protein of interest was linked to the ubiquitin promoter in a plasmid and a plant material transformed by any one of numerous methods known to those skilled in the art for introducing heterologous genes into plant tissue. The plant tissue containing the gene was selected, cultured and grown, and seed harvested. The seed is dehulled and degermed, then air dried to about 15% moisture. It is then fractioned through a series of sieves and select fractions containing the majority of the germ aspirated at higher air velocity to obtain a germ-rich fraction. The germ was defatted and protein was extracted with hexane and air dried. Purification of the protein varies according to the protein being produced, and such methods are well known to those skilled in the art.

The following is provided by way of example and is not intended to limit the scope of the invention. Those skilled in the art will appreciate that variations in the procedures and materials described are possible and yet still fall within the scope of the invention

EXAMPLE 1

Commercial Production of Avidin

We have produced in transgenic maize seed the glycoprotein, avidin, which is native to avian, reptilian, and amphibian egg white. Transcription of the heterologous gene is driven by the maize ubiquitin promoter, and translation is targeted to the endoplasmic reticulum surface because of an attached signal sequence. A transformant showing high-level expression of avidin was selected. Southern blot data revealed that four copies of the gene are present in this transformant. The foreign protein represents >2% of aqueous soluble extracted protein from populations of dry seed, a level higher than any heterologous protein previously reported for maize. In seed, greater than 55% of the extractable transgenic protein is present in the embryo, an organ representing only 12% of the dry weight of the seed. This ndicates that the ubiquitin promoter previously was considered to be constitutive, in this ase shows a strong tissue preference in the seed, and further to the germ of the seed. Subcellular localization of the mature protein is primarily localized to the intercellular paces.

For production, transgenic maize plants were grown in isolation plots up to one half acre in size. An interesting trait of the transgenic plants expressing avidin is that the presence of the gene correlates with partial or total male sterility. Because of this trait, no homozygous plants have been obtained Seed populations from transgenic plants were maintained by outcrossing and segregate 1:1 for the trait. In generations T2–T4, avidin expression remained high at 2.3% (230 mg/kg seed) of extractable protein from seed, though it varied from 1.5–3.0%. However, levels of expression did not appear to depend on pollen parent or growing location. Production fields of this male sterile line yielded approximately 230 mg avidin protein per kg of seed. Processing steps of harvested seed that included drying ears to 13% moisture at up to 40° C., shelling ears for seed storage, and cracking and flaking kernels prior to protein extraction generated no apparent loss of avidin activity. Some seed was dry milled to enrich for embryos, the fraction which contained most of the avidin, to test the efficacy of embryo enrichment in large scale purification applications. Cracked and flaked kernels stored at −29° C. or 10° C. for up to three months showed no significant loss of avidin activity. Commercial processing steps of harvested seed also generated no apparent loss of activity. Storage at higher temperatures lowered activity after one to three weeks. Avidin activity in maize seed extracts showed no significant susceptibility to endogenous protease activity. The protein was purified to greater than 90% purity by affinity chromatography after extraction from mature maize seed. Physical characterization of purified maize-derived avidin demonstrated that the N-terminal amino acid sequence and biotin binding characteristics are identical to the native protein with near identical molecular weight and glycosylation.

Avidin is a glycoprotein found in avian, reptilian and amphibian egg white. Its gene expression is induced by progesterone as well as by certain events, such as tissue trauma, the presence of toxic agents, and bacterial and viral infections. Induction appears to be primarily at the transcriptional level. The protein avidin is composed of four identical subunits, each 128 amino acids long, the amino acid sequence of which has been known since 1971 [11]. the CDNA of the chicken oviduct avidin gene was documented by Gope et al. [12] and a genomic lone was isolated Keinanen et al. [13]. More recently, Keinanen et al. [14] reported on a family of closely related avidin genes from chicken.

Avidin forms a particularly strong, non-covalent bond with biotin. It is this property of avidin that is responsible for its commercial value, because it allows for detection of protein and nucleic acid molecules that have biotin incorporated into their structure. The customary source for commercial production of avidin has been chicken egg white, a method of relatively high production costs.[2]

Abbreviations: HABA, 4-hydroxyazobenzene-2'-carboxylic acid; 2-ME, beta mercaptoethanol; DTA, ethylenediamine tetraacetic acid; PMSF, phenylmethanesufonyl fluoride; PBS, phosphate buffered line; SDS-Page, sodium dodecy sulfate polyacrylamide gel electrophoresis; TBST, Tris buffered saline Tween; BSA, bovine serum albumin; ECI, enhanced chemilumincscence: pNPP, para nitrophenyl phosphate.

Materials and Methods

Construction of plasmids used for transformation. The chicken egg white avidin cDNA was reported by Gope et al. [12]. The amino acid sequence was reverse translated into nucleic acid sequence utilizing a preferred maize codon usage table (GCG, assembled by Mike Cherry, Stanford University). From this computer-generated synthetic sequence, overlapping, complementary oligonucleotides with compatible restriction site termini were designed, then annealed and ligated to yield the maize optimized gene. The barley alpha amylase signal sequence [15] was also synthesized (using overlapping, complementary nucleotides) with maize-preferred codons. Compatible restriction sites between these two gene fragments were ligated, with the signal sequence at the 5' end of the avidin gene. The resultant signal sequence/avidin segment was cloned, as a BamH I/EcoRI fragment, into the vector pGEM3Zf+, a product of Promega Corporation (Madison, Wis.), to generate plasmid PHP5142. A BamHI/HpaI fragment containing the signal sequence/avidin region was isolated and cloned into a plasmid (PHP5038) derived from pBlueScript SK+, as a backbone (Stratagene, La Jolla, Calif.). In this plasmid, the signal sequence/avidin gene fragment was inserted between the maize ubiquitin 5' region, which includes the promoter, the first exon and first intron [56, European Patent # 0 342 926], and the potato proteinase inhibitor II (PinII) transcription terminator region [7]. The resultant plasmid is PHP5168 (FIG. 1A).

The 560 base pair coding sequence of the bar gene from *Streptomyces hygroscopicus* was removed as a PvuII/Hincll fragment and ligated into a Bluescript SK+-based plasmid (PHP289). This plasmid contained from previous cloning steps the double 35S promoter [16], the Tobacco Mosaic Virus omega' leader [17], the intron from the maize alcohol dehydrogenase gene [4] and the potato pinli terminator [7] The resultant expression cassette for herbicide resistance is plasmid PHP610 (/FIG. 1B)

Transformation and tissue culture. An established callus line derived from a single immature embryo of the "Hi-II" maize germplasm was transformed using particle bombardment-mediated transformation with helium-powered particle acceleration device, PDS 1000 (Bio-Rad, Hercules, Calif.) Tissue showing a friable type-II embryogenic morphology was sieved through 710 $\mu$m mesh prior to co-transformation with equimolar amounts of the avidin gene (PHP5168) and the bar selectable marker gene (PHP610), according to the procedures of Tomes et al. [19]. Transformants expressing the bar gene were selected in the presence of bialaphos (3mg $l^{-1}$), according to the protocol of Register et al. [20]. Co-transformants that also expressed the avidin gene were identified by ELISA screening of the selected colonies. Multiple plants (T0 generation) were regenerated from avidin-expressing colonies, transferred to the greenhouse and assayed for avidin expression in leaf tissue. T1 seed was obtained by outcrossing, with the T0 plants as the female parent and a non-transformed inbred line (PHN46) as the male parent.

Light microscopy. Light microscopy was performed on embryo pieces fixed overnight in 0.5% glutaraldehyde/3% paraformaldehyde in 0.01 M sodium phosphate buffer pH7.2, dehydrated in an ethanol series and embedded in LR White acrylic resin (EM Sciences, Fort Washington, Pa.). Sections 1–2 microns) were cut on a Reichert Ultracut S ultramicrotome. Slides were blocked with 2% powdered milk and 1% BSA plus 1% normal goat serum (NGS) in Tris buffered saline with Tween-20 (TBST; 0.01 M Tris, pH 8.0; 0.15 M sodium chloride; 0.05% Tween-20) overnight, incubated at room temperature for 1 h with primary antibody (anti-avidin serum antibody, ICN) diluted 1:100 in blocking buffer, washed 3×10 min in TBST, incubated at room temperature for 1 h with secondary antibody (goat anti-rabbit TRITC conjugate, Sigma Chemical Co.) diluted 1:100 in blocking buffer, washed 3×5 min in TBST, 2×1 min in water. Slides were viewed with phase contrast or epifluorescence on a Leica DMRB microscope and photographed on Fujichrome 1600 slide film. Images were scanned using Photoshop (Adobe) software and labeled with Freehand (Macromind) software.

Tissue printing. Tissue prints of developing kernels (approximately 40 days after pollination, DAP, [21]) were made on nitrocellulose that had been wet with distilled water and air dried. Prints were either stained with India Ink or reacted with anti-avidin polyclonal antibodies (ICN) diluted 1:1000 in TBST. Secondary antibodies (Sigma Chemical Co.) were goat anti-rabbit IgG conjugated to alkaline phosphatase and were diluted 1:1000 in TBST. Negative controls consisted of either no primary antibodies or maize of the same genotype transformed with a different gene. Incubation conditions were as described by Fritz et al. [2 1 ]. Images were scanned and labeled as above.

Southern blotting. High molecular weight genomic DNA was isolated [42] from lyophilized young maize leaves from which the mid-vein had been removed. Digested DNA (10 $\mu$g per lane) was electrophoresed in 0.8% agarose gels and transferred to Hybond-N nylon membranes (Amersham) and hybridized as described by Lowe et al. [23]. $^{32}$P-labeled probes were prepared using a Rediprime kit (Amersham). The avidin probe was a 470 base pair fragment of the avidin gene from the plasmid shown in FIG. 1A. The phosphinothricin resistance gene was probed with a 567 base pair fragment of the bar gene as shown in plasmid PHP610 in FIG. 1B. Hybridization was detected on Amersham Hyperfilm using two screens. Exposure times varied with the intensity of the signal on the blot, but typically overnight. Images of the films from the Southern blots were scanned using the Photoshop (Adobe) software package, and the lanes labeled using Microsoft Powerpoint.

PCR. DNA was isolated from leaf tissue pieces the size of a small paper punch using the method of Jhingan [28]. DNAs were resuspended in a small volume of Tris:EDTA (pH 8.0) in a 10 mM, 1 mM ratio. Prior to PCR, the DNA samples were heated at 65° C. for 10 min. All PCR reactions were performed with a 25 $\mu$l volume in 96 well plates and contained 2 $\mu$l isolated DNA, 240 $\mu$M dNTPs (Pharmacia), 1 unit Taq polymerase (Boehringer Mannheim Biochemicals, BMB, Indianapolis, Ind.), and 1×reaction buffer (BMB). Oligonucleotide primers (1 $\mu$M each), 20 base pairs in length, that corresponded to sequences in the avidin gene, amplified a DNA fragment approximately 450 base pairs in size. Amplification was achieved using an initial melting step at 94° C. for 1.5 min., then 35 cycles of 94° C. for 40 seconds, annealing at 62° C. for 60 seconds, and lengthening at 72° C. for 1 minute in a Biotherm oven.

Scoring of male sterility. When ear shoots on plants in the field began to show silk, the tassels were examined for extrusion of anthers. Plants that showed no anther extrusion were scored as completely sterile. Plants with extrusion of a few anthers that contained no pollen were scored as shedders or partially sterile plants. Plants were observed two days after the initial scoring to confirm the phenotype.

Biochemical materials. The ECL (Enhanced Chemiluminescence) kit was purchased from Amersham (Arlington Heights, Ill.). The 2-iminobiotin agarose resin and 4-hydroxyazobenzene-2'-carboxylic acid (HABA) were obtained from Sigma Chemical Co. (St. Louis, Mo.). The rabbit polyclonal antibodies raised against avidin were obtained from ICN (Costa Mesa, Calif.). Horseradish peroxidase-conjugated secondary antibodies were from BMB. N-Glycosidase A was purchased from Seikagaku America (Ijamsville, Md.). All other chemicals were of reagent grade.

ELISA for quantitation of avidin. ELISAs were conducted on extracts of leaves or seed. Samples were ground in a mortar and pestle (leaves) or a coffee grinder (seeds) and extracted in 50 mM PBS pH 7.0 containing 0.05% Tween-20. Total protein was quantified using the Bradford assay [25]. ELISAs were typical sandwich style in which the microtiter plates were coated with rabbit anti-avidin antibody (Vector Labs, Burlingame, Calif.), the avidin protein was captured overnight at 4° C., was reacted with biotinylated anti-avidin antibody (1 h, 37° C.) then with Zymed streptavidin conjugated to alkaline phosphatase (1 h, 37° C.). The alkaline phosphatase was detected with para nitrophenyl phosphate (pNPP) at 1 mg ml$^{-1}$ in 10% diethanolamine buffer at 37° C. Plates were read after 0.5 and 1 h at 405 nm on a microplate reader, Spectra Max 250 using the Softmax Pro software (Molecular Devices, Sunnyvale, Calif.).

SDS-PAGE and immunoblot analysis. Proteins were analyzed by SDS-PAGE using 4–20% gradient gels (Novex, San Diego, Calif.) and the buffer system of Laemmli [26]. Gels were stained with Coomassie blue or transferred to ImmpbilonP-PVDF (Millipore) for immunoblot analysis as previously described [27]. Immunoblots were blocked for 1 h in TBST containing 5% nonfat dry milk (Blotto). Blots were incubated overnight in affinity-purified anti-avidin polyclonal antibodies at a dilution of 1:100. The blots were washed 3×10 min in TBST, then incubated for 1 hour in goat anti-rabbit secondary antibody conjugated to horse radish peroxidase at a dilution of 1:5000. After washing 3×10 mm in TBST, the blots were developed using Amersham's enhanced chemiluminescence (ECL) protocol.

Affinity-purification of anti-avidin polyclonal antibodies. Rabbit polyclonal antibodies were affinity purified [28] using Immobilon-P transfer strips containing purified chicken egg white avidin (Sigma Chemical Co.). Briefly, Immobilon-P transfer strips with bound purified chicken avidin were incubated overnight with 100 μl of serum diluted in TBS. The strips were washed 3×10 min with 50 mM Tris (pH 7.4), 500 mM NaCl then washed 3×10 min with 50 mM Tris (pH 7.4), 150 mM NaCl. The polyclonal antibodies were eluted from the strips with 50 mM glycine (pH 2.5). The purified antibodies were neutralized with 1 M Tris (pH 8.0).

Deglycosylation of avidin. Two μg of purified maize-derived avidin or native chicken avidin (Sigma Chemical Co.) were dissolved in a buffer containing 10 mM sodium acetate (pH 5.1), 0.375 M sodium isothiocyante, and 50 mM B-mercaptoethanol. N-glycosidase A (NGA) was added to a final concentration of 0.2 units ml$^{-1}$, and incubated at 37° C. for 18 to 24 hrs. The reaction was stopped by boiling for 2 min in SDS-PAGE sample buffer, then analyzed by SDS-PAGE.

Biotin inhibition of HABA binding to avidin. One hundred μg of purified maize-derived or native chicken avidin were diluted to 1 ml with phosphate buffered saline (0.01 M NaPO$_4$ pH 7.0; 0.15 M NaCl, PBS) for the avidin activity assay. Twenty-five μl of 10 mM HABA (pH 7.6) [29] were added to the 1 ml of PBS containing avidin solution, and the solution read at 500 nm on a Beckman DU-640, a reading representing 0% inhibition. One μl of 0.125 mg ml$^{-1}$ biotin was then added to the solution, and after mixing thoroughly, read again at 500 nm, and repeated until no change was observed in the OD. The normalized absorbance value was obtained by subtracting from all the absorbance values, the value at which the absorbance change stopped. The 0% inhibition value was set to 1.0 and all the other absorbance values were scaled accordingly.

Separation of maize embryo (germ) and endosperm. Five hundred grams of dry kernels (12% moisture) were placed in a polyethylene bag and moisture-conditioned at 4° C. to the preselected moisture content (MC) by adding water to 16% MC using a 16 h holding time, increasing to 21% MC in an additional 1.5 h, and to a final 24% MC in 15 min. After conditioning, the kernels were passed through a horizontal custom-made dehuller/degermer, which was operated at 16,000 rpm, at a feed rate of approximately 18 kg h$^{-1}$.

The dehulled and degermed seed was air-dried at room temperature to 15% moisture and fractionated through a series of sieves (Standard Testing Sieves, Fisher Scientific, Philadelphia, Pa.) (Table 1). Fractions from sieves No. 5 through 12 were collected and aspirated to remove hulls using a Test Model Duo-aspirator (Carter Day International, Minneapolis, Minn.). The fraction retained by sieve No. 5 consisted mostly of whole or partially broken kernels. The majority of free embryos were retained by sieves No. 5 and 7. These two embryo fractions were treated at higher air velocity to aspirate the embryo-rich fraction away from heavier debris. The combined embryo-rich fractions accounted for 77% of the total embryo amount with purity of approximately 35%. To obtain high-purity embryos, the free embryos were hand-picked. The moisture content of various fractions was determined by completely drying 2 to 5 grams of each sample at 125° C. for 6 h, and calculating the loss in mass as percent moisture.

Effect of protease inhibitors on avidin stability. Dry maize kernels (12 % MC; 500 g per batch) were first cracked using a roller mill (Ferrell-Ross, Oklahoma-City, Okla.), then flaked to 0.3 mm thickness using Roskamp flaking rolls (Model K, Roskamp Mfg., Inc., Waterloo, Iowa.). The particle size distribution of flaked material was determined by sieving (see Table 1).

Twenty grams of flaked kernels were extracted with 200 ml of Tris-HCI pH 7.9 containing 500 mM NaCl, 1 mM CaC$_2$ with stirring for 30 min at ambient temperature. One extraction was performed in the absence of protease inhibitors (control) and one in the presence of a protease inhibitor mixture containing 10 mM 2-mercaptoethanol (2-ME), 5 mM ethylenediamine tetraacetic acid (EDTA), 0.1 mM phenylmethanesulfonyl fluoride (PMSF), and 0.2 mM Diazo-N-acetyl-N-Leu-MeO. EDTA and 2-ME were added at the beginning of the extraction, and PMSF and diazo-N-acetyl-N-Leu-MeO were added 15 min after the extraction began. The insoluble residue was separated by centrifugation at 20,500× g for 25 min at 0° C. The supernatant was filtered through four layers of cheese cloth. The extracts were sampled at 0, 3, 6 and 22 h for biotin binding activity [30]. and for protein integrity on western blots. For a positive control, chicken egg white avidin (Sigma Chemical Co.) was dissolved in the extraction buffer and samples were taken as above for activity assays.

Proteins from the above sampling times were separated by SDS-PAGE on 10% gels. Following electrophoresis, the gel was soaked for 10 min in 1X Bjerrum and Schafer-Nielsen transfer buffer [30]. Proteins from the presoaked acylamide gel were transferred onto a 0.2 μm nitrocellulose membrane using a semidry-electroblotting apparatus (BioRad, Richmond, Calif.). The nitrocellulose membrane was incubated in 10% (w/v) dry milk in PDS-T at room temperature for 30 min followed by overnight incubationin anti-avidin antibody diluted 1:1000 in blocking buffer. Excess antibody was removed by washing the membrane 4× with PBS-T. The membrane was incubated with Protein-A gold (Bio-Rad) diluted 1:100 in blocking buffer until pink protein bands were visible.

Storage stability. Seven 500 gram batches of maize kernels were cracked and flaked as described in the previous section. Flaked samples, 50 g each, were placed in zip-lock bags and stored at each of four different temperatures (−29, 10, 25 and 37° C.) up to 95 days. Avidin stability experiments were performed in triplicate; three 50 g samples per time and per temperature. To determine the activity of avidin, a 20 g sample was taken from each of the three 50 g bags at the specified time and extracted with 200 ml of the extraction buffer as described above.

Purification of avidin from maize. Thirty grams of transgenic maize seed were ground for 1 min in a coffee grinder. The meal was extracted for 1 h at 4° C. with constant stirring at a 5:1 (w/v) ratio in a buffer containing 50 mM sodium carbonate (pH 11.0), 500 mM NaCl, 5 mM EDTA, and 0.05% Tween-20. The extraction mixture was centrifuged at 10,000 rpm for 15 min in a Sorvall GSA rotor at 4° C. The supernatants were removed and filtered through 4 layers of cheese cloth. The filtrate was centrifuged at 10,000 rpm for 15 min in a Sorvall SA 600 rotor at 4° C. The supernatant was recovered and the pH adjusted to 10.5, then centrifuged at 11,000 rpm for 30 min in an Eppendorf Type 16f6-38 rotor. The supernatant was incubated with 5 ml of 2-iminobiotin agarose [32] for 1 h at 4° C. with constant agitation, the resin placed in a column and washed with 150 mL of a solution containing 50 mM sodium carbonate (pH 11.0), 2.0 M NaCl, 5 mM EDTA, and 0.05% Tween-20. The resin was washed again with the same buffer but without Tween-20. Avidin was eluted from the resin wiwth 20 mM acetic acid. Each fraction (2 ml) was neutralized with 0.1 M NaOH. The fractions which contained avidin were dialyzed against ddH$_2$O overnight.

Results.

Construction of expression cassettes containing the avidin and bar genes. A gene optimized for expression of avidin protein in maize was generated by annealing and ligating overlapping, complementary synthetic oligonucleotide sequences that were based on codon usage bias for maize. Additionally, a DNA sequence encoding the barley alpha amylase signal sequence [15] was generated via the same approach, and was ligated to the 5' terminus of the avidin gene in such a way that normal cellular processing of the translated pre-avidin protein would accurately cleave the signal sequence yielding mature avidin protein. This signal sequence was included based on the prediction that higher levels of avidin expression could be obtained if newly synthesized avidin protein was targeted to the extracellular compartment. The expression cassette (FIG. 1A) included in addition to the avidin segment, the maize ubiquitin promoter [5, 6] and the pinII terminator from potato [7]. The ubiquitin promoter is considered a constitutive promoter that shows limited tissue specificity we have shown here that it drives high levels of expression particularly directed to the embryo.

The expression cassette for the selectable marker gene, phosphinothricin phosphotransferase (ppt), which encodes resistance to the herbicide bialaphos, [bar; 44; FIG. 1B], included the 35S promoter derived from Cauliflower Mosaic Virus sequences [16] and the pinII terminator from potato [7]. Expression cassettes similar to this have been shown to confer resistance to bialaphos in maize tissue culture (see also, [33])

Generation of avidin-expressing, transgenic plants. Regenerable embryogenic calli transformed by particle bombardment were selected on bialaphos for 10 weeks. Resistant calli were subjected to ELISA analysis to confirm the expression of the avidin gene. Plants initially regenerated from selected embryogenic tissue (T0) were used as females in crosses with an untransformed inbred as the pollen donor. Regenerated T0 plants were screened for high expression of avidin in leaf tissue (>0. 1% of extracted protein). Our goal, however, was to produce avidin from seed. Therefore, T1 seed from an event showing high leaf expression, was screened to confirm high levels of expression in seed tissue as well. Avidin expression was segregating in the T1 generation, and some seed was negative. However, expression in positive seeds ranged from 2.1–5.7% of aqueous extractable protein (determined by ELISA).

Characterization of the high-expressing avidin transform ant.

Molecular biology. Five individual T1 plants from this event were analyzed for their DNA structure (FIG. 2). The linked avidin and bar genes were segregating as a single unit among individuals in these populations, and it was not surprising to find the genes present in only three plants. The avidin gene copy number was estimated at three to five as determined by DNA blot hybridization using an SphI digest of genomic DNA When double digests using SphI and SpeI were conducted to determ ine the size of the plant transcription unit, five separate fragments could be identified, none of which were the same size as the original plasmid-derived plant transcription unit—two were smaller and three were larger (FIG. 2A). Similarly, the selectable marker gene, bar, was present at four copies. In double digests probed with the bar gene (FIG. 2B), a band of the correct size was present, but these plants also contained two other transcription unit sizes, one smaller and one larger than the original construct. The avidin and bar inserts appear to be inherited as a single linkage unit, and it is not clear which of the inserts is active in transcription and translation. Similar integration patterns were present in all plants examined.

Figure 3B:
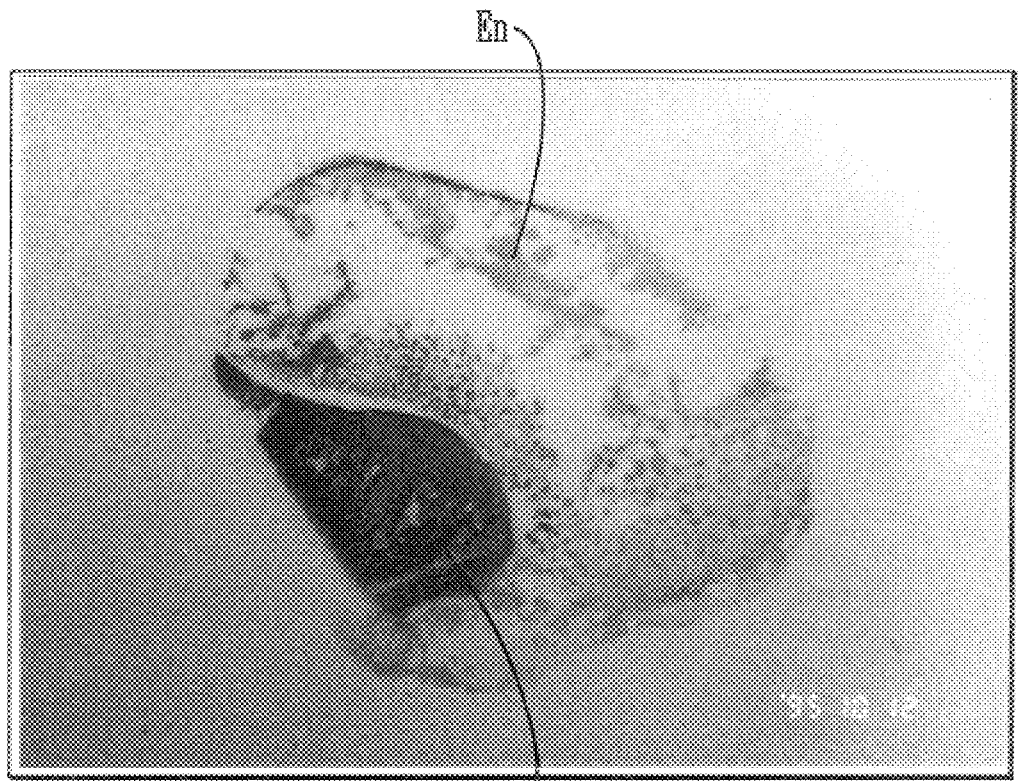
Figure 3C:
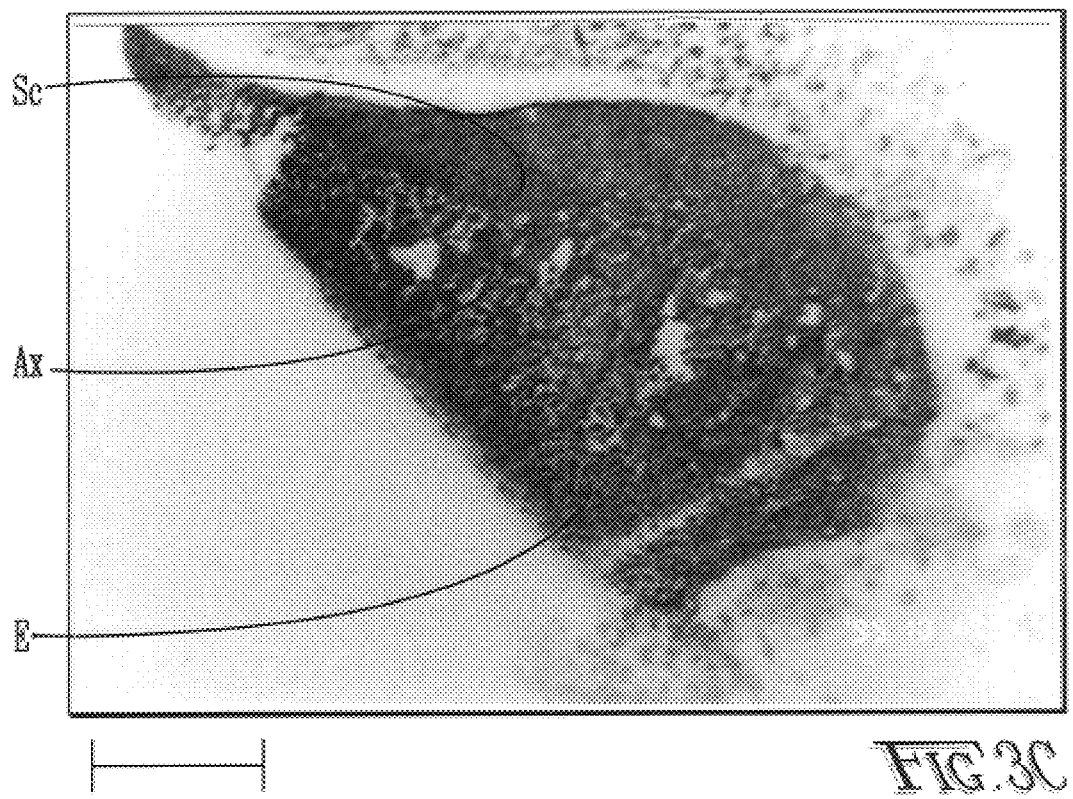
Figure 3D:
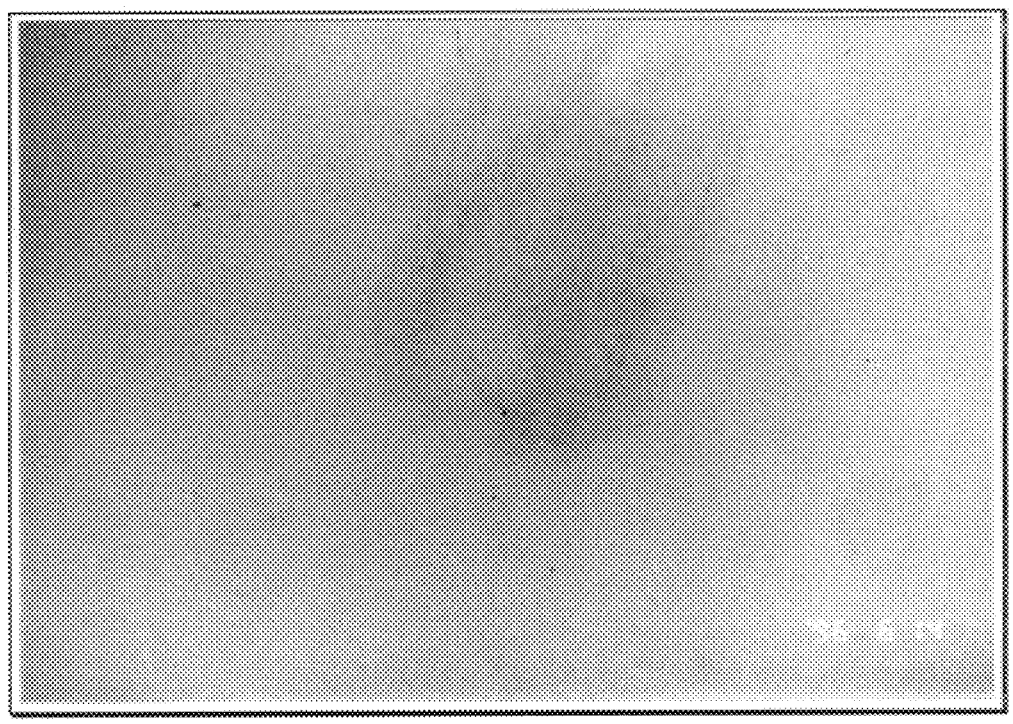

Cell biology. In seeds of the transgenic maize plants, avidin protein is primarily localized to the embryo. This was determined through tissue printing (FIG. 3) and embryo versus endosperm extraction and quantitation of avidin protein. Within the embryo, tissue prints reveal that the scutellum is the major sink of avidin, with the embryo axis accumulating somewhat lesser amounts (FIGS. 3B, 3C). In extraction studies, the endosperrn, which represents approximately 80% of the total kernel weight, contains just 22% of the avidin activity found in whole kernels. An additional 5% of the activity is present in the hulls (pericarp), also shown by tissue printing. The embryo, however, contains at least 55% of the avidin protein found in whole dry seed. The avidin protein balance indicates that 18% of the total activity is not accounted for and possibly is lost during dry milling.

Figure 4A:
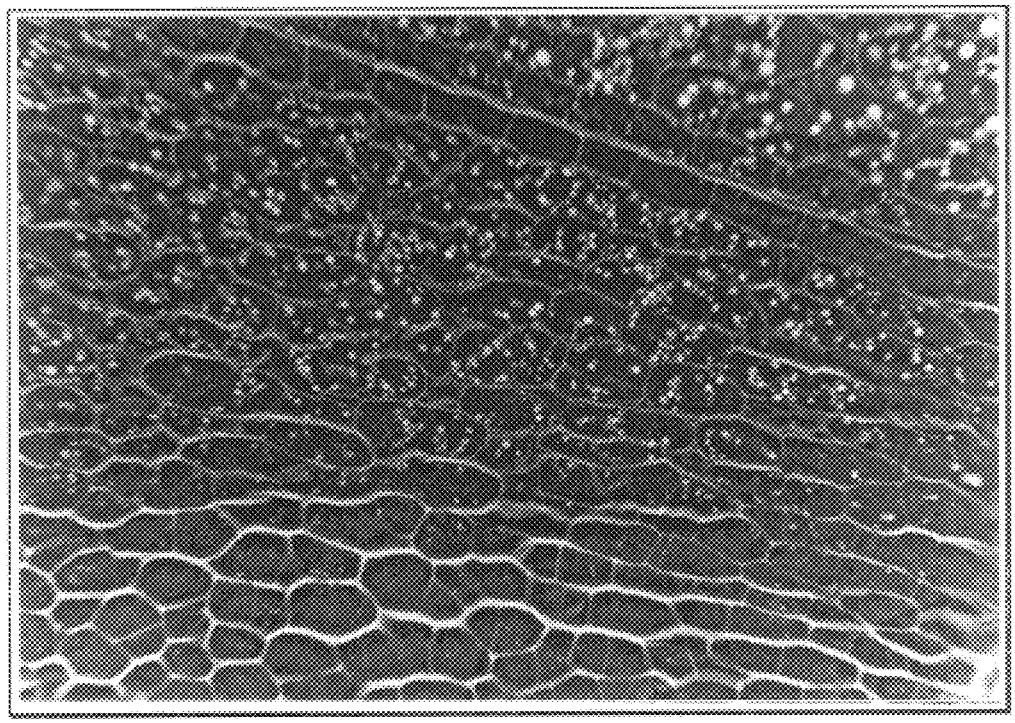
FIG. 4: Localization of avidin protein in the embryo at the light microscope level. A. Phase contrast image of embryonic axis. B. Rhodamine (TRITC) fluorescence of same image as in A. Double arrows mark similar locations in each image. Bar represents 10 $\mu$m.

In situ localization experiments were performed on thin sections of embedded embryos using anti-avidin primary antibodies and TRITC fluorescently labeled secondary antibodies (FIG. 4). Phase contrast images of embedded sections showed excellent preservation of the cellular structure (FIG.

Figure 4B:

4A). Fluorescence was present in cell walls indicating that avidin is primarily localized to that organelle (FIG. 4B).

Genetics. Biolistic transformation of maize was performed using the Hi-II tissue culture line [18]. This genotype is highly regenerable, flowers and usually sets seed in the greenhouse in the T0 generation. However, because T0 plants regenerated from tissue culture often exhibit problems with fertility and/or pollen transmission of the transgene, an outcross was performed in this first generation with pollen from an elite Pioneer inbred line, PHN46. The seed from this first outcross was planted in a winter nursery for seed increase.

This avidin-expressing line lost resistance in the T1 generation to the herbicide on which it was originally selected in culture. Thus, a different scheme was required to identify transformed plants in the field in subsequent generations. Therefore, we pursued polymerase chain reaction (PCR) as an alternative method to select avidin-positive plants. Additionally, however, many of the plants exhibited male sterility, and a 97.5% correlation was observed between presence of the avidin gene (by PCR) and the male sterile/limited fertility phenotypes (Table 3). This same phenomenon also occurred in other avidin-positive lines, making it highly unlikely that the phenotype was a result of foreign gene insertion into a native gene required for pollen development The male sterile phenotype was subsequently used for scoring of transformed plants. In production fields in 1995 and one in 1996. PCR results indicated that 50–55% of plants in one field contained the avidin gene, the expected result from crossing a hemizygous female plant with a wild-type pollen donor.

Production. A program was designed to scale up the production of seed from this avidin-positive line, the goal of which was to obtain sufficient material from which to purify commercial quantities of recombinant avidin protein. It was critical to determine if the expression of avidin varied when the plants were grown in different locations or if expression was reduced in later generations because of gene inactivation.

Taking advantage of winter nurseries, we initiated a backcross program with this transgenic avidin-positive maize line to establish the transgene in two high quality elite Pioneer inbreds, that when crossed, will produce a high-yielding hybrid. The phenotype of T3 generation plants was vigorous and seed yield was increased above the T1 generation. The high levels of avidin protein in this transformed line were associated with male sterility, i.e., the anthers lacked pollen. Therfore, for seed production, vigorous inbred or hybrid lines and fertile sibling plants (Table 4) were used as pollen bearing parents.) Ears were harvested only from plants showing loss of fertility, and the seed was shelled and bulked.

The data (Table 3) show the levels of avidin present in extracts from seed produced in four different planting locations and over four generations (T1–T4). Quantitation of avidin levels in production seed lots was done by ELISA analysis. Because the avidin gene can only be inherited from the female and is hemizygous in those plants, the harvested seed contains a near 50:50 mixture of avidin positive and negative kernels and quantitative estimates incorporate both phenotypes. The expression of avidin was at a level that would yield an estimated 150–300 mg avidin per kg of harvested seed (Table 3), the average being 230 mg per kg of seed. Because the pollen donors utilized to date are the same in locations where protein levels vary (compare locations 1, 3 and 4 in Table 3), they do not appear to be a factor in variation of protein yield in the seed. The various growing locations were chosen to test whether environmental conditions might affect protein accumulation in the seed. In this context, several observations were made. First, the gene encoding for avidin is not silenced in later generations (as demonstrated in expression at T3 and T4). Second, the variation in avidin as percent of extractable protein among locations was not attributable to any obvious genetic or environmental condition. The level of avidin expression is slightly lower in T3 generation seed but this range of variation in T3 seed is similar to that observed in seed from a single location (Hawaii) over several generations.

Because only 50% of the seed recovered from sterile plants carries the heterologous gene, the plants in subsequent production fields must be screened for phenotype, either using PCR or DNA isolated from leaf samples, or by scoring for male sterility. The avidin-expressing transgenic plants produced at least one ear with approximately 300–400 kernels, i.e., a 300–400-fold increase. Therefore, 1 kg of transgenic seed should yield approximately 150–200 kg, assuming 50% segregation in the seed source. We produced 160 kg of transgenic avidin seed in 1995 from 1 kg of starting material, a 300-fold increase. This yield can be attributed to good growing conditions, high plant quality, efficiency in scoring male sterility and successful pollination.

Figure 5:
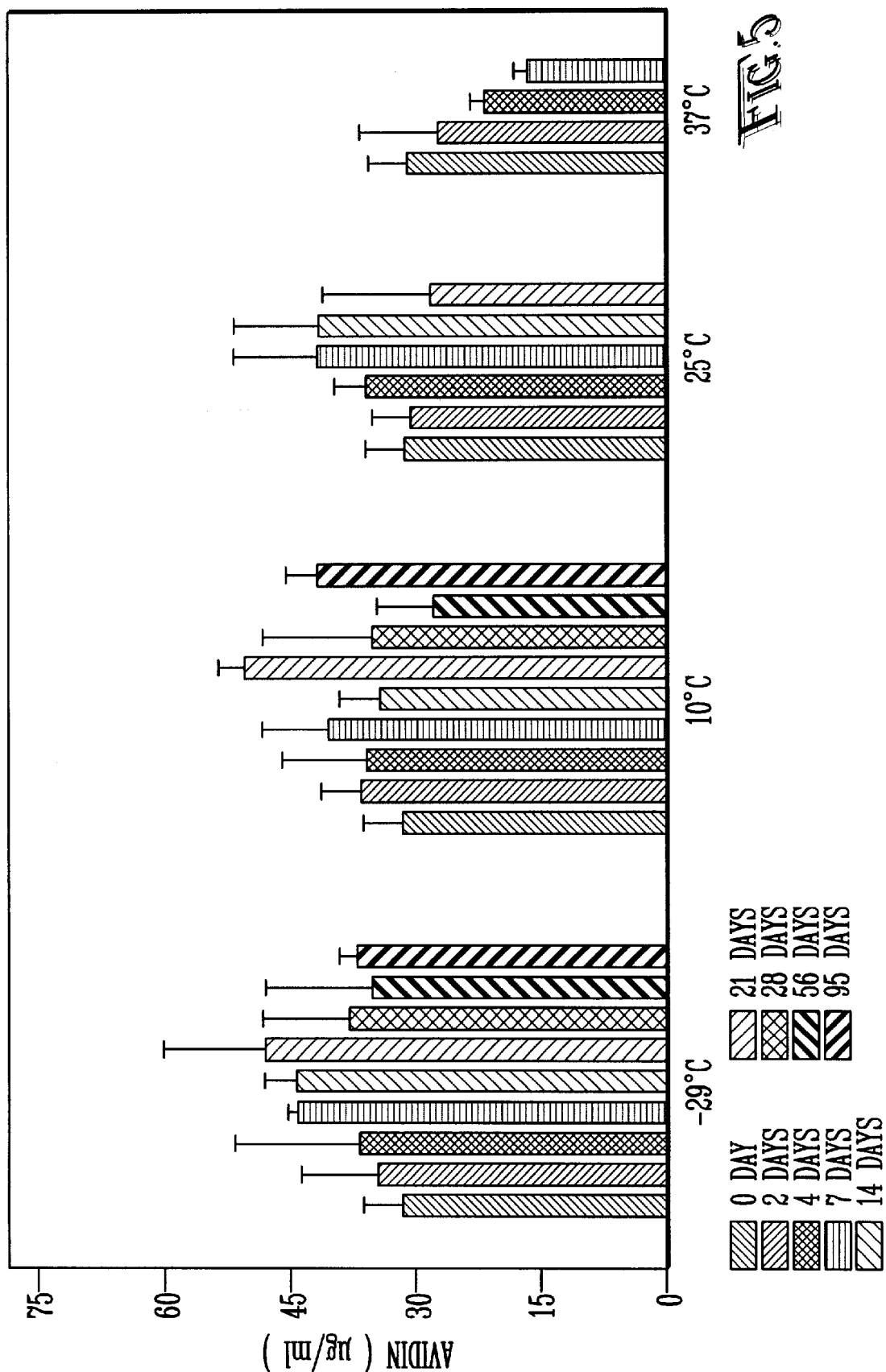
FIG. 5: Effect of temperature on avidin stability during storage of flaked maize seed. Maize seed was processed by cracking and flaking, then stored at the indicated temperatures. Triplicate samples were extracted and analyzed for avidin binding activity after the times (in days) shown by the shaded bars. Bars represent means with standard deviations indicated by the vertical bars.

Processing. Seed drying and processing as currently practiced require an elevated temperature which potentially could destroy avidin activity in the whole kernel as well as in the flaked material. Therefore, the effect of temperature on avidin activity was investigated. Avidin in whole kernels was stable and could withstand temperatures up to 50° C. for at least 7 days without loss of activity. This allows the seed to be dried using conventional practices which typically operate at temperatures of 41° C. for three days. In addition, our data (FIG. 5) indicate that avidin retains its original activity in the processed flaked material for up to 95 days at −29° C. and 10° C. Likewise, no significant change in avidin activity was measured when flakes were stored at 25° C. for up to 21 days. However, almost 50% of the initial avidin binding activity was lost when flaked material was stored at 37° C. for 7 days. The sample-to-sample variability (large standard deviation) was most likely caused by the variability in the activity assay when used on crude seed extracts. In any event, the thermostabilty of avidin in flakes and whole kernels allows significant flexibility in terms of storage, processing and transportation conditions to ensure integrity during delivery to the desired purification site.

Extraction and purification. We have established that equal amounts of avidin protein can be extracted from seed subjected to either cracking and flaking, or to grinding into flour (data not shown). Therefore, the less labor-intensive flaking was selected as the method of choice for seed processing prior to the protein extraction step.

For commercial scale purification, avidin is extracted in a sodium bicarbonate/sodium chloride buffer (pH 11) containing Tween-20 and EDTA. The extract contains a complex mixture of proteins. as shown by Coomassie Blue staining of proteins electrophoretically separated in a 10% SDS-polyacrylamide gel (FIG. 6A lanes 2 and 3). Avidin is affinity purified from this complex mixture by incubating the extract with 2-iminobiotin agarose [32]. The binding is efficient, as no avidin protein is detected by western blot analysis of the column void (FIG. 6B, void). As determined by ELISA and estern blot analyses, avidin is quantitatively eluted from this column in two fractions. (FIGS. 6A and 6B).

The monomeric molecular weight of native avidin from chicken egg white is 17,600 Da [12]. It is a glycoprotein with a single carbohydrate chain attached to the Asn-17 amino acid residue. In addition to the major glycosylated form of avidin, two minor molecular weight variants are visible on a stained gel or western blot when >2 μg of purified maize-derived avidin are loaded per lane (FIGS. 6A and 6B). One minor variant has a molecular weight of 12,500 Da and comigrates with the deglycosylated form (see FIG. 9). A second minor variant has a molecular weight of approximately 9,000 Da. When sequencing was performed on this smallest variant, it was found that the N-terminal 42 amino acids of the mature protein including the glycosylation site were missing.

Figure 7A:
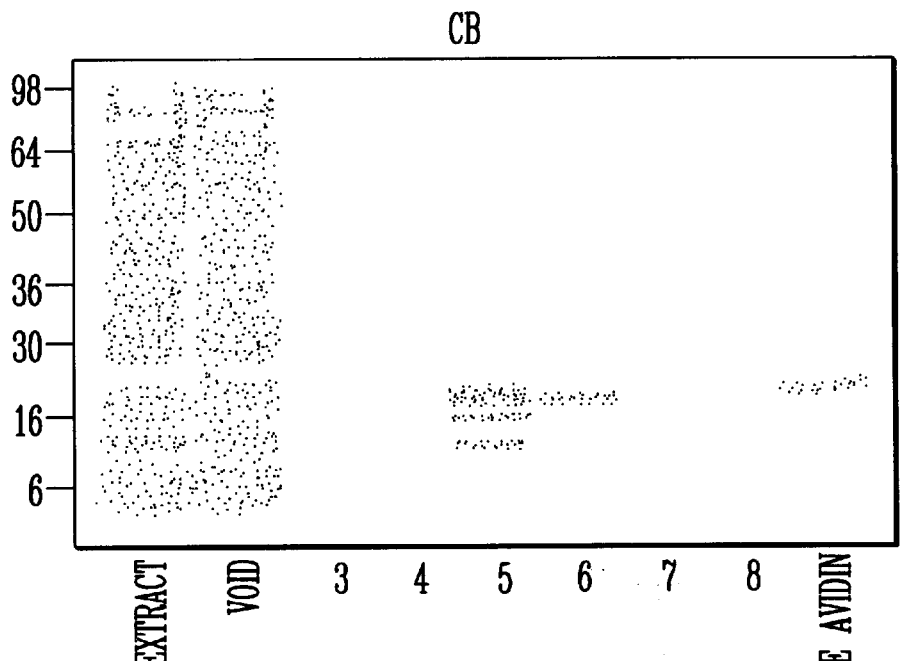
FIG. 7: Purification of recombinant avidin from maize seed extract. A. Coomassie Blue (CB) stained 4–20% polyacrylamide gel of: Lanes:—10 $\mu$l of avidin positive corn extract (Extract), 10 $\mu$of column void (Void), 4 $\mu$l of column elution fractions 3–8 (lanes 3–8). and 2 $\mu$g of native avidin (native avidin). B. Immunoblot stained with affinity-purified polyclonal antibody against avidin: Lanes—$\mu$l of avidin positive corn extract (Extract).10 $\mu$l of column void (Void), 2 $\mu$l of column elution fractions 3–8 (lane 3–8), and 1 $\mu$g of native avidin (native avidin). Molecular weight standards ($\times 10^{-3}$) are indicated on the left.
Figure 7B:
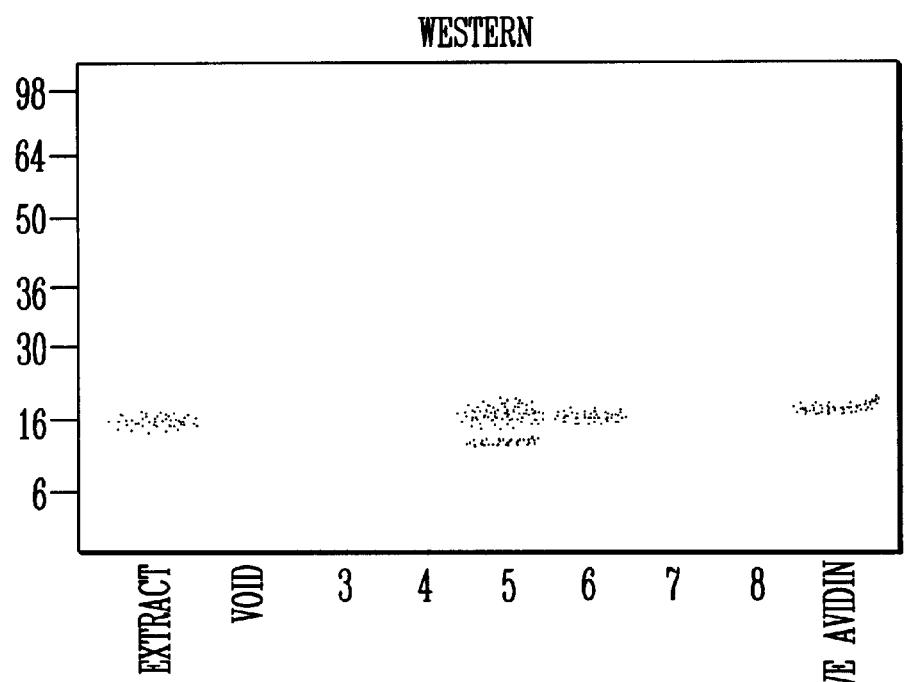
Figure 8A:
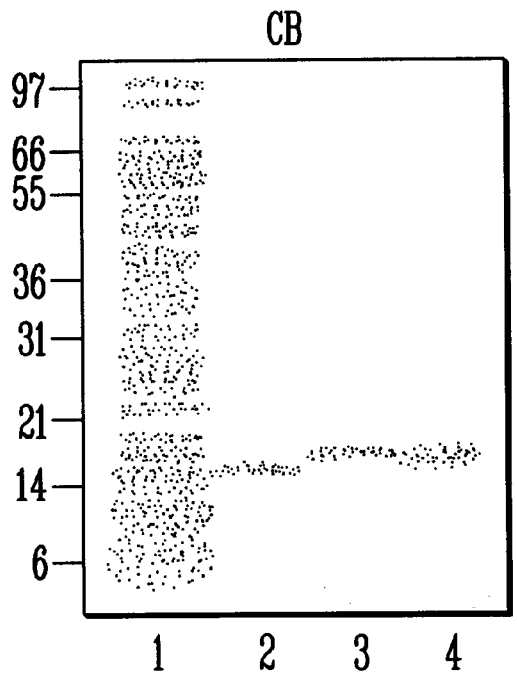
FIG. 8: Comparison between recombinant avidin and native avidin. A. Coomassic blue (CB) stained 4–20% polyacrylamide gel of: Lanes: 1.20 $\mu$g avidin-positive maize seed extract; 2.1 $\mu$g of recombinant avidin; 3.1 $\mu$g of native avidin; and 4.0.5 $\mu$g each of native and recombinant avidin. B. Western blot (WB) stained with affinity-purified polyclonal antibody raised against avidin. Lanes: 1.20 $\mu$g of avidin positive seed extract; 2.0.5 $\mu$g of recombinant avidin: 3.0.5 $\mu$g of native avidin and 4.0.5 $\mu$g each of recombinant and native avidin. Molecular weight standards ($\times 10^{-3}$) are indicated on the left.
Figure 8B:
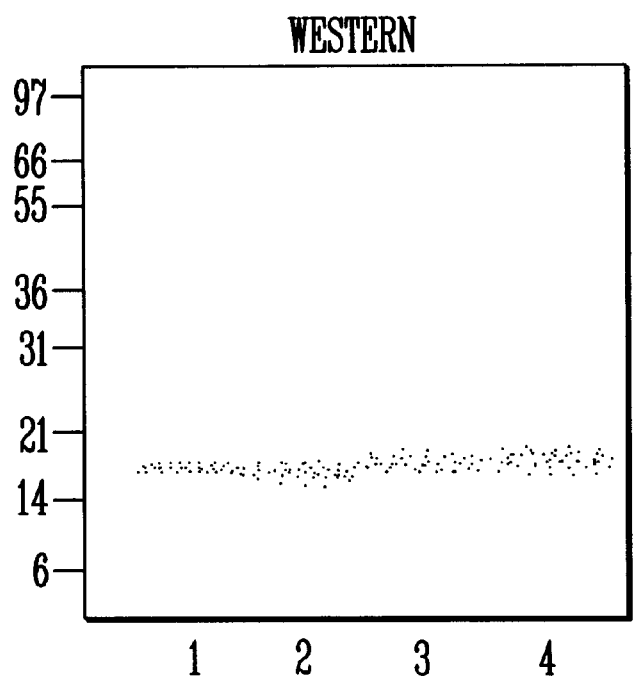

The source of the 9,000 Da fragment is not known, and we hypothesized that it could be due to a proteolysis occurring during initial grinding and extraction steps. If so, addition of protease inhibitors to the extraction buffer might reduce this minor proteolysis of avidin. However, activity assays show that at 22 hours after extraction, avidin activity is not significantly different in the presence or absence of protease inhibitors (Table 5). In addition, western blot analysis of these same fractions showed no degradation product that reacted with anti-avidin antibodies (FIG. 7), even when the gels were over-loaded. This indicates that extracted avidin is quite stable and the proteolytic fragment may be the result of a cellular event prior to seed grinding.

Figure 6:
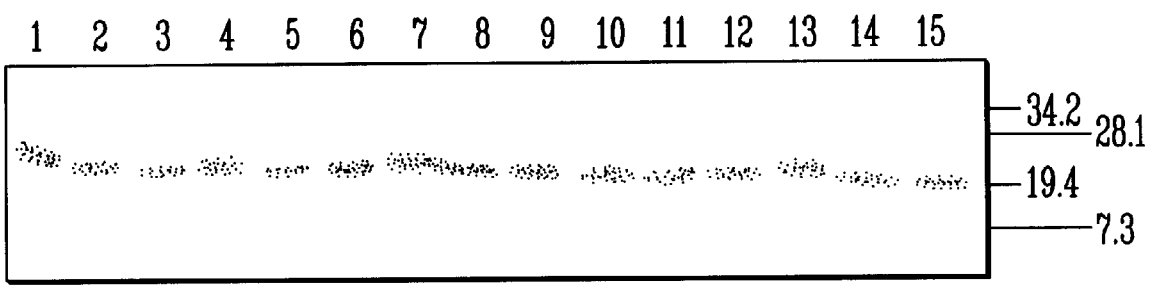
FIG. 6: Western blot of extracts of flaked maize seed in the presence of and absence of protease inhibitors. Lanes: 1, 4, 7, 10 and 13—native avidin after 0, 1, 3, 6 and 22 h without inhibitors. Lanes: 2, 5, 8, 11 and 14—maize extracts after 0, 1, 3, 6 and 22 h without inhibitors. Lanes: 3, 6, 9, 12, and 15—maize extracts after 0, 1, 3, 6 and 22 h with inhibitors.
Figure 9:
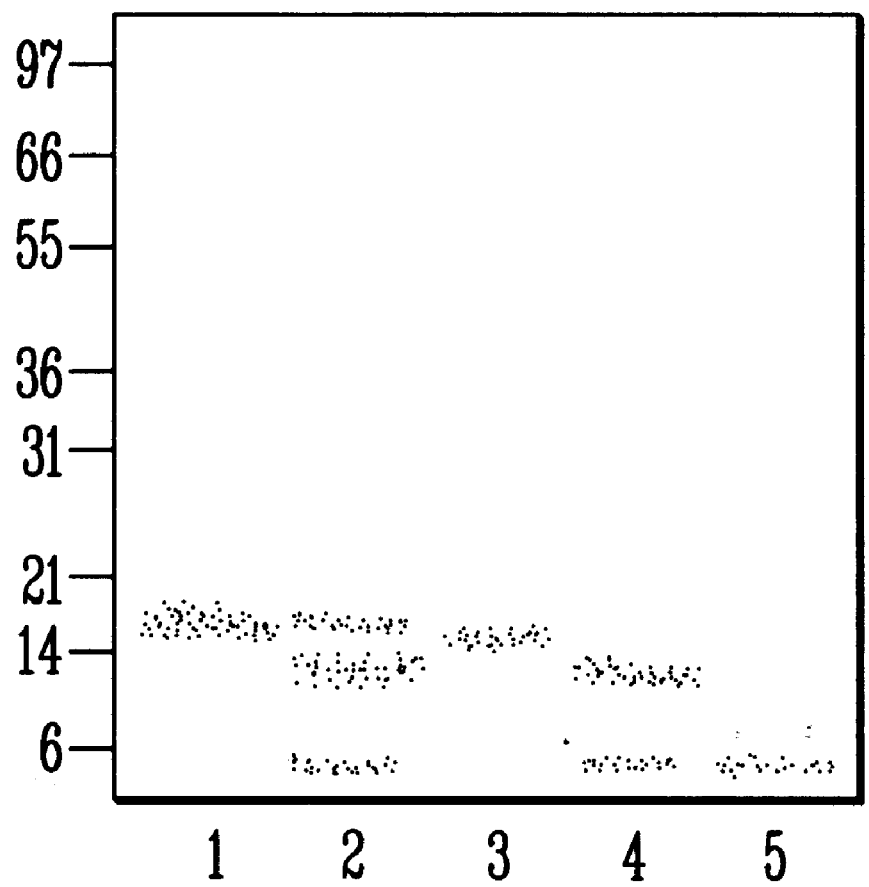
FIG. 9: Deglycosylation of avidin. Native avidin (2 $\mu$g) was incubated overnight at 37° C. in the absence (lane 1) or presence (lane 2) of 0.5 m units of N-glycosidase A (NGA). Recombinant avidin (2 $\mu$g) was also incubated overnight at 37° C. in the absence (lane 3) or presence (lane 4) of 0.5 m units of NGA. Lane 5 contains 0.5 units of NGA incubated overnight at 37° C. The 4–20% polyacrylamide gel was stained with Coomassie blue. Molecular weight standards ($\times 10^{-3}$) are indicated on the left.

Physical characterization of avidin from transgenic maize seed. A comparison of the physical characters of the native and maize-derived avidins was performed and the amino-terminal sequence of the two proteins as determined by Edman degradation [34] was revealed to be identical (Table 5). Egg-white and maize-derived avidins were also compared on stained SDS-polyacrylamide gels and western blots (FIG. 6). The protein in maize seed extract and in purified form has a molecular weight of 16,800 Da (FIG. 6 lanes 1 and 2) based on migration of the standards in this gel system. This is approximately 800 Da smaller than the native chicken protein [17] (FIG. 6 lanes 3 and 4). However, when proteins from both sources were digested with N-glycosidase A (NGA), the resulting deglycosylated forms were identical with a molecular weight of approximately 12,500 Da (FIG. 9). The smaller band in the lanes containing enzyme-treated samples is a protein from the enzyme preparation itself (compare lanes 3 and 5 to 6 in FIG. 9). These data combined with the N-terminal sequence data (Table 6) strongly suggest that the primary structure of the two avidins is identical.

In vivo, avidin exists as a homotetramer and its activity is to bind biotin to protect avian and reptilian eggs from pathogen invasion. Based upon this biotin-binding property, an analog of biotin, HABA, is utilized for the quantification of activity. Using the HABA binding assay, estimates of total avidin amounts in the fractions eluted from the affinity column were identical to estimates made by ELISA. When competitive binding studies were performed for avidin with biotin and HABA, the native and maize-derived avidins produced identical inhibition constants (Ki, Table 6). The deglycosylated form of chicken egg-white avidin binds biotin as well [35], though it is not known if this is also true for the maize-derived recombinant avidin.

In additional experiments, other physical characteristics of the proteins were addressed (Table 6). Using ochterlony double diffusion, antigenic identity of native and recombinant avidins was confirmed (data not shown). The isoelectric point (pI) of the native and maize-derived avidins is at least 10, the highest (most basic) value for pI that can be experimentally determined (Table 6). This value correlates well with the calculated value of 10.4.

The localization of avidin to the cell wall matrix was not surprising as the gene was fused to a signal sequence, which targeted the protein to the endoplasmic reticulum during translation. In plants, the default pathway for proteins transported through the endoplasmic reticulum is secretion, because a protein's ultimate subcellular location depends on factors other than just the presence of the signal sequence, including topological information on the protein itself. For example, specific N- or C-terminal peptides direct vacuolar proteins to receptors that target them to the vacuole. When these sequences are removed, the proteins are secreted. These topological signals were not engineered onto the avidin gene construct and in this case, the protein was secreted.

TABLE 1

Schedule for increasing moisture content (MC) of dry maize seed.

| Moisture content (% wb$^A$) | Holding time (h) |
|---|---|
| From Initial MC to 16 | 16 |
| 16 to 21 | 1.5 |
| 21 to 24 | 0.25 |

$^A$wb = wet base

TABLE 2

Size of sieve openings and fraction of maize seed retained by the sieves.

| Sieve number | 5 | 7 | 12 | 25 | 50 | 100 | flow through |
|---|---|---|---|---|---|---|---|
| Sieve openings (mm) | 4.00 | 2.83 | 1.68 | 0.71 | 0.30 | 0.15 | <0.15 |
| Retained fraction (% of dry weight) | 2.5 | 9.7 | 20.8 | 31.6 | 18.5 | 16.4 | 0.5 |

TABLE 3

Correlation of male sterile/limited fertility phenotype with presence of the avidin gene as determined by PCR.

| PCR Result | # Fertile | # Partially Sterile | # Sterile |
|---|---|---|---|
| + | 1 | 6 | 32 |
| − | 40 | 0 | 1 |

TABLE 4

Expression level of avidin protein as a percent of aqueous-extractable protein in T1 through T4 generations of maize seed.

| Location$^A$ | Avidin as % of extracted protein | Pollen parent | mg Avidin per kg seed |
|---|---|---|---|
| greenhouse | 0.8$^B$ (T1) | PHN46$^G$ | 80 |
| 1 | 3.0 ± 0.40$^C$ (T2) | PHN46 | 300 |
|  | 1.5 ± 0.16$^D$ (T3) | 3394 | 150 |
|  | 2.4 ± 0.10$^E$ (T4) | +sibs | 240 |
| 2 | 1.9 ± 0.23$^D$ (T3) | 3162 | 190 |
| 3 | 1.8 ± 0.19$^D$ (T3) | 3394 + sibs | 180 |

TABLE 4-continued

Expression level of avidin protein as a percent of aqueous-extractable protein in T1 through T4 generations of maize seed.

| Location[A] | Avidin as % of extracted protein | Pollen parent | mg Avidin per kg seed |
|---|---|---|---|
| 4 | 3.0 ± 0.11[F] (T3) | 3394 + sibs | 300 |
| average | 2.3% | | 230 |

[A]Locations: 1. Hawaii winter nursery, Hawaii isolation field, (T3); Hawaii isolation field, (T4); 2. Texas winter nursery, (T3); 3. Johnston, IA isolation field, (T3); 4. Nebraska isolation field, (T3).
[B]Mean of 10 individuals.
[C]Mean of two bulk populations of 20 seeds each, three replicates each; ± standard error of the mean.
[D]Mean of six populations of 20 seeds and three bulk populations of 50 seeds each; ± standard error of the mean.
[E]Mean of two bulk populations of 10 seeds each; ± standard error of the mean.
[F]Mean of six bulk populations of 20 seeds each; ± standard error of the mean.
[G]PHN46, Pioneer elite inbred; 3394, Pioneer hybrid; sibs, fertile siblings from previous out-cross.

TABLE 5

The effect of protease inhibitors on avidin stability

| Time (h) | Without inhibitors (μg ml$^{-1}$) | With inhibitors (μg ml$^{-1}$) | Control avidin (μg ml$^{-1}$) |
|---|---|---|---|
| 0 | 32.0 | 32.5 | 88.2 |
| 1 | 41.1 | 27.1 | 62.6 |
| 3 | 23.8 | 31.4 | 61.1 |
| 6 | 32.3 | 32.9 | 60.6 |
| 22 | 21.0 | 29.7 | 59.6 |

TABLE 6

Summary of physical characterization data for native and maize-derived avidins.

| Avidin Source | N-Terminal Sequence | MW | Glycosylation | Ki | antigenic similarity | pI |
|---|---|---|---|---|---|---|
| egg white | ARKCSLTGKWTNDLGSXMTI | 17.6 k Da | yes | 3.2 uM | identical | 10 |
| maize-derived | ARKCSLTGKWTNDLGSXMTI | 16.8 k Da | yes | 3.3 uM | identical | 10 |

EXAMPLE 2

Commercial Production of β-Glucuronidase

We used rGUS as a model protein to investigate the recovery of recombinant protein from transgenic corn. This systems was selected because of adequate expression levels of rGUS, simplicity and sensitivity of the enzyme assay, and the availability of the transgenic corn seed in sufficient amounts to address various aspects of downstream processing. In this study we are reporting some of the factors in the downstream processing of transgenic corn that affect rGUS activity, purity, and the recovery yield.

MATERIALS AND METHODS

Production of Transgenic Corn

The transgenic corn kernels were provided by Pioneer Hi-Bred International (Johnston, Iowa.). The transgenic corn producing rGUS was prepared by using transformation, selection, and plant regeneration methods reported by Hood et al. (36).

Degermination

The germ was separated from the endosperm by a dry-milling process (3). Five hundred grams of dry corn kernels (12% moisture) were placed in a polyethylene bag and moisture conditioned at 4° C. to the preselected moisture content (MC) by adding water according to the schedule shown in Table 7. After conditioning the kernels were passed through a horizontal custom-made dehuller/degermer operated at 16,000 rpm with a feed rate of approximately 300 g/min. The dehulled and degermed kernels were air-dried at ambient temperature to around 15% moisture and fractionated through a series of sieves (No. 3.5, 5, 7, 12, 25, and 50 Standard testing Sieves, Fisher Scientific, Philadelphia, Pa.). The fractions retained by sieves No. 3.5 through 12 were collected and aspirated to remove the hulls using a Test Model Duo-aspirator (Carter Day International, Minneapolis, Minn.). The fraction retained by sieve No. 3.5 consisted mostly of whole or partially broken kernels. The majority of the germ was retained by sieves No. 5 and 7. The germ fractions from sieves No. 5 and 7 were aspirated at higher air velocity to obtain a germ-rich fraction. The combined germ-rich fractions contained 77% of the initial germ amount.

Distribution of rGUS in the Corn Kernel Tissue

Corn kernels (100 g) were soaked in deionized water for two days. The hulls, endosperm, and germ were manually separated. Each fraction was air-dried at ambient temperature and ground with a coffee grinder (Salton/Maxim Housewares Inc., Mt. Prospect, Ill.). rGUS activity and the moisture content of each ground sample were determined. rGUS activity was determined using the assay described by Jefferson and Wilson (37). One unit (U) of rGUS activity was defined as the amount of enzyme that converts one nmole of p-nitrophenyl β-D-glucuronide per minute at pH 7.0 and 37° C.

Storage and Heat Stability

Dry corn kernels (12% moisture, 500 g per batch) were cracked using a roller mill (Ferrel-Ross, Oklahoma City, Okla.), then flaked to 0.3 mm thickness using Roskamp flaking rolls (Model K, Roskamp Mfg., Inc., Waterloo, Iowa.). Seven 500-gram batches of flaked corn kernels were placed in zip-lock bags and stored at each of four different temperatures for up to 95 days. The storage stability study was performed in triplicate; three 50-g samples per time and per temperature. To determine the activity of GUS, a 20-g sample was taken from each of the three 50-g bags at the specified time and extracted with 200 ml of 20 mM Tris-HCl pH 7.9 containing 500 mM NaCl and 1 mM CaCl$_2$. Extraction was carried out using a paddle mixer at ambient temperature for 30 min.

The heat stability of rGUS at temperature above 50° C. was studied by heating corn kernels in a convection oven Isotemp 500 series (Fisher, Pittsburgh, Pa.). Ten-gram batches of corn kernels were placed in separate aluminum pans and placed in the oven at four different temperatures (50, 70, 90 and 125° C.) for up to eight hours. The heat stability study was performed in duplicate; two 10-g samples per time and per temperature. Heat-treated corn kernels were ground using a coffee grinder prior to extraction. Three-gram ground samples were extracted with 30 ml of 50 mM NaPl pH 7.5 and GUS activity in the extract was determined.

rGUS Extraction

A portion of the germ sample prepared by the degermination process was defatted by using a Soxhlet apparatus. Forty grams of full-fat germ were extracted with 300 ml of hexane for five hours, and then air-dried at ambient temperature to remove the hexane.

All samples (flaked kernels, full-fat germ and defatted germ) were ground using a coffee grinder before protein extraction. The samples were extracted at 1:4 or 1:10 solid-to-liquid ratio with 50 mM NaPi buffer of pH 7.5. The extraction was carried out for 15 min at ambient temperature by using a magnetic stirrer for mixing less than 50-ml and a paddle mixer for greater than 50-ml volumes. After stirring, the suspension was centrifuged at 26,000 g for 25 min at 0° C., and then filtered through a 4-layer of cheese cloth. The extract was assayed for GUS activity (36) and protein (37).

The efficiency of rGUS extraction was qualitatively examined by staining the spent solids with 0.1% X-Gluc (5-bromo-4-chloro-3-indolyl-$\beta$-D-glucupyranoside) solution. After the extraction, spent solids were separated by centrifugation at 26,000 g, rinsed extensively with water to remove the remaining rGUS, and dried at ambient temperature. To a 100 mg of washed and dried solids, 2 ml of 0.1% X-Gluc solution were added and the suspension was incubated at 37° C. for 30 min. The presence of a blue precipitate (stain) in the solids indicated incomplete extraction of rGUS.

The extraction yield was estimated by SDS-PAGE followed by a Western blot analysis. A 500-$\mu$l aliquot of the 2x SDS-PAGE sample buffer was added to 100 mg of washed and dried solids. The mixture was boiled for 5 min, and 15-$\mu$l aliquots were loaded on the gel. SDS-PAGE was carried out on a 10% resolving gels at a constant voltage of 150 V (38). Following the SDS-PAGE, the gel was soaked for 10 min in Bjerrum and Schafer-Nielsen transfer buffer (39). Protein bands from the presoaked acrylamide gel were transferred onto a 0.2-$\mu$m nitrocellulose membrane at a constant voltage of 10 V for 30 min using a semidry-electroblotting apparatus (BioRad, Richmond, Calif.). The nitrocellulose membrane was incubated in a blocking solution containing 10% milk diluent solution (Kirkegaard and Perry, Gaithersburg, Md.) in PBS-T at ambient temperature for 30 min followed by an overnight incubation with poly-clonal anti-GUS in the blocking solution. The excess antibody was removed by washing the membrane with PBS-T. The membrane was then incubated with Protein-A gold solution (Bio-Rad, Hercules, Calif.). The immunoreactive protein bands were enhanced by silver staining (Bio-Rad, Hercules, Calif.) and quantified by densitometry.

Purification rGUS was purified from ground kernels, full-fat germ and defatted germ using a three-step chromatography. Ground corn kernels (75 g), full-fat germ (7.5 g), and defatted germ (7.5 g) samples were extracted with 50 mM NaPi buffer pH 7.5 (buffer A) at 1:4 or 1:10 solid-to-liquid ratio as described in the previous section. Fifteen ml of DEAE-Toyopearl (Supelco, Bellefonte, Pa.) resin in buffer A were added to the centrifuged and filtered extract to adsorb (capture) rGUS. The slurry was mixed with a magnetic stirrer for 15 min at ambient temperature, filtered through a funnel-supported No. 1 filter paper, and washed with 400 ml of buffer A. The washed DEAE resin was packed into a glass column with an inside diameter of 1.5 cm. The adsorbed rGUS was eluted with 0.3 M NaCl in buffer A. The fractions containing rGUS activity were combined, ammoniumsufate (AS) was added to a final concentration of 1 M, and the solution was filtered through a 0.45 $\mu$filter. The filtered solution was applied to a 12 ml of octyl-Sepharose column (Pharmacia, Piscataway, N.J.) pre-equilibrated with buffer A containing 0.3 M NaCl and 1 M ammonium sulfate (buffer B). The column was first washed with 15–20 column volumes (CV) of buffer B followed by buffer A (9–13 CV) containing 150 mM NaCl and 500 mM AS to elute the loosely bound protein. rGUS was eluted by applying 200 ml of NaCl/AS (105 mM /350 mM to 52 mM/175 mM) gradient in Buffer A. The flow rate during sample loading, washing, and elution was maintained at 2 ml/min. The fractions containing GUS activity were combined and diafiltered against distilled water using a Centriprep-30 concentration unit (Amicon, Beverly, Mass.). The diafiltered sample was applied to a second DEAE-Toyopearl column pre-equilibrated with Buffer A. After loading the sample, the column was washed with 3 CV of the same buffer, and rGUS was eluted with 200 ml of 0 to 0.3 M NaCl gradient in Buffer A. The purity of rGUS was estimated by densitometry of protein bands on the SDS-PAGE gel (38), which was stained with Coomassie blue.

RESULTS AND DISCUSSION

Storage and Heat Stability

The handling of harvested corn includes drying the kernels to a final moisture content below 15% and storing the corn at different temperatures depending on the required length of storage, relative humidity of air, the kernel moisture content, and the end application. Drying, storage, and processing (milling) temperatures of transgenic corn is of a particular importance because integrity and activity of the recombinant protein must be preserved. For example, during drying as well as in the commercial corn milling kernels could be exposed to temperatures as high as 100° C. At the end, the primary (upstream) processing of transgenic corn (milling, degermination, fractionation, oil extraction, etc.) will probably be performed at a site different than the bioprocessing (downstream processing) plant, and processed corn may require different temperature regime for transporting and storing than that established for commercial grain. For these reasons, we have investigated the storage and heat stability of rGUS in processed corn (flaked kernels) and whole kernels, respectively.

Figure 10A:
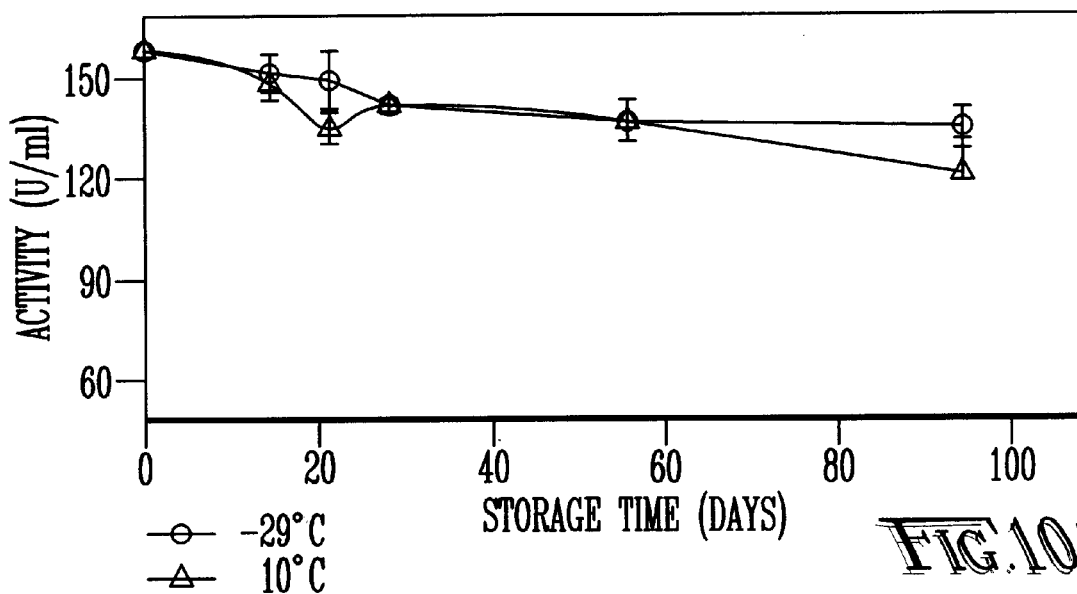
FIG. 10: are graphs showing storage stability of rGUS in flaked corn.
Figure 10B:
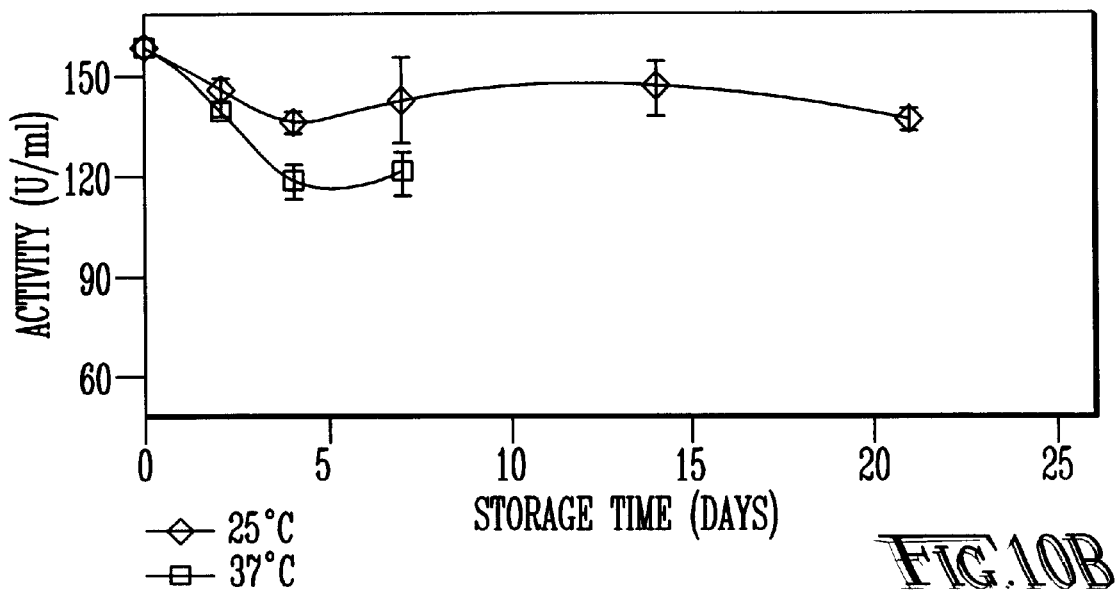

Storage stability study (FIG. 10) showed that no significant loss of rGUS activity occurred when flaked kernels were stored at −29, 10, or 25° C. for up to 2 weeks. When flaked kernels were stored at 37° C. for one week, 23% of the initial rGUS activity was lost. Storing the flaked kernels at −29 and 10° C. for up to 3 months resulted in 14% and 23% loss of rGUS activity, respectively. At ambient temperature (25° C.), a sample spoilage was observed after three weeks and a loss of 13% of the initial GUS activity was measured. Therefore, flaked kernels can be transported and stored at ambient temperature (25° C.) for a period of less than two weeks without affecting rGUS activity. If necessary, flaked kernels can be stored for up to two months at 10° C. A similar storage stability data were obtained for recombinant avidin in transgenic corn (3).

Figure 11A:
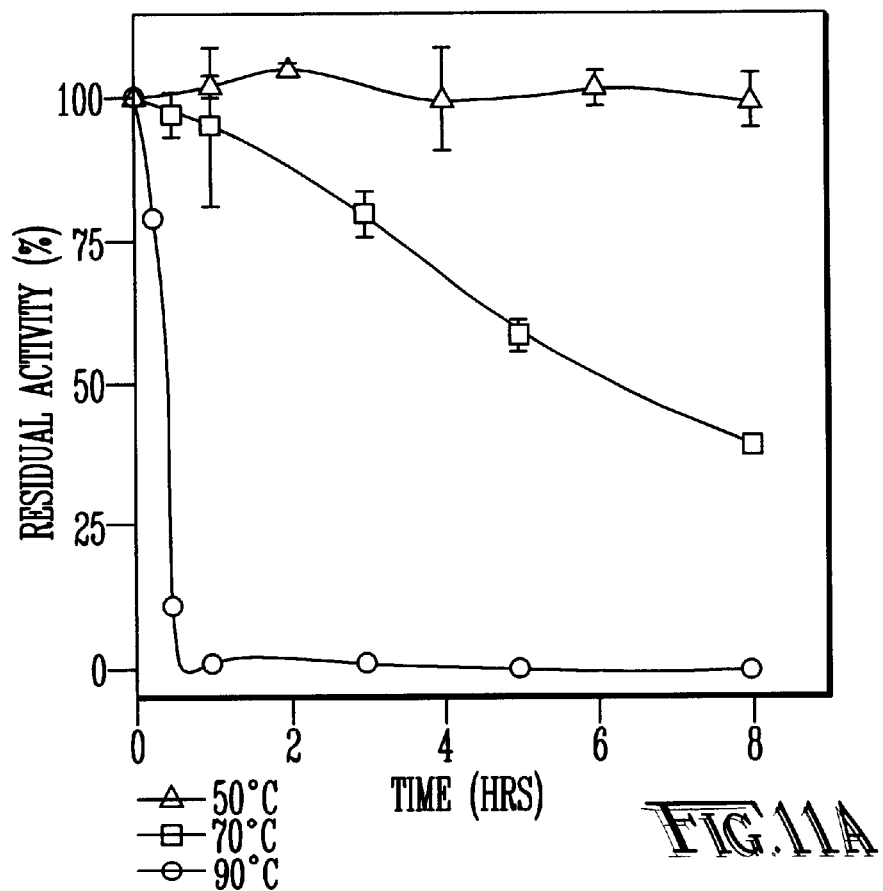
FIG. 11: is graph depicting heat stability of rGUS in corn kernels.
Figure 11B:
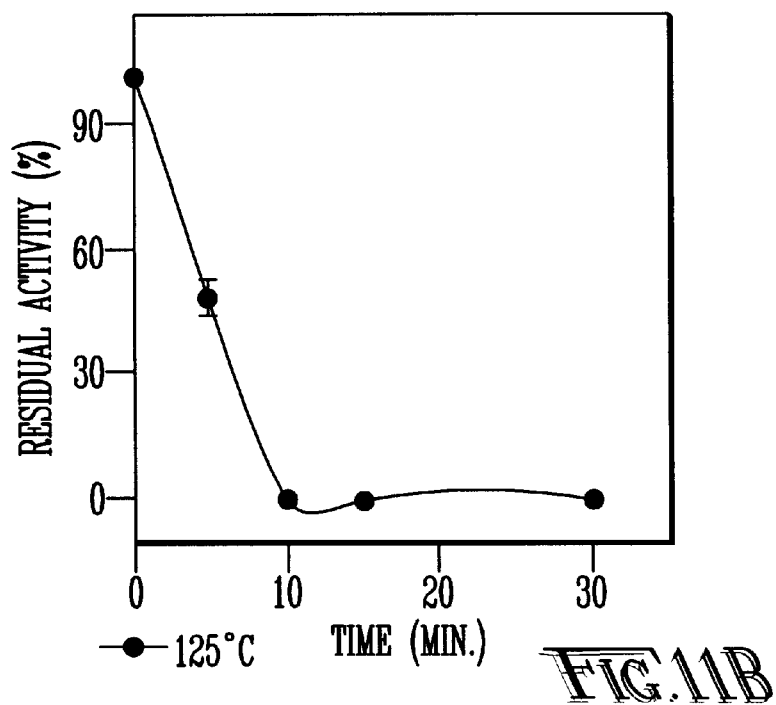

The heating of whole kernels with initial MC of 12.6% at 50° C. for up to eight hours did not affect rGUS activity (FIG. 11). The prolonged heat stability study indicated that rGUS activity in the kernels was fully retained for up to six days at 50° C. (data not shown). Heating at 70° C. for one hour also did not significantly affect rGUS activity, but after 8 hours 60% of its initial activity was lost. No residual rGUS activity was observed after heating the kernels for one hour at 90° C. and for 10 min at 125° C.

The heat stability results obtained in the laboratory were validated on a large scale. During the processing of 1,000 kg of transgenic corn in a custom-milling plant located in Grinnell, Iowa, the corn was exposed for a short time (less than 1 min) to 90° C. The milled corn was bagged at approximately 50° C., transported at ambient temperature (30° C.) for two hours to Iowa State University, and then stored overnight at 10° C. before the rGUS activity was determined. Sampling of milled transgenic corn revealed no loss of rGUS activity, which indicated that lab-scale heat-stability data could be used to predict the effect of the storage and processing temperature on the recombinant protein.

Extraction of rGUS

To determine the effect of extraction parameters on rGUS activity, eight process variables were screened using a quarter factorial design experiment. Based on the analysis of screening experiments, the following extraction conditions were used in the subsequent studies: 1) 50 mM NaPi buffer of pH 7.5; 2) minimum of 1:4 solids-to-buffer ratio; and 3) mixing for at least 15 min at ambient temperature. The screening experiments revealed that particle size distribution of the ground corn (i.e. flaked vs. milled corn) and the mixing speed did not significantly affect the extraction yield. In addition, the presence of 0.5 M NaCl, 0.05% (v/v) of Tween-20 and a cocktail of protease inhibitors consisting of 10 mM ME, 5 mM ethylenediamine tetraacetic acid (EDTA), 1 mM phenylmethyl sulphonyl fluoride (PMSF), 0.2 M dioazoacetyl D,L-norleucine methyl ester (diazo AcNleOMe) in the extraction buffer did not increase the recovery of rGUS activity.

Figure 12:
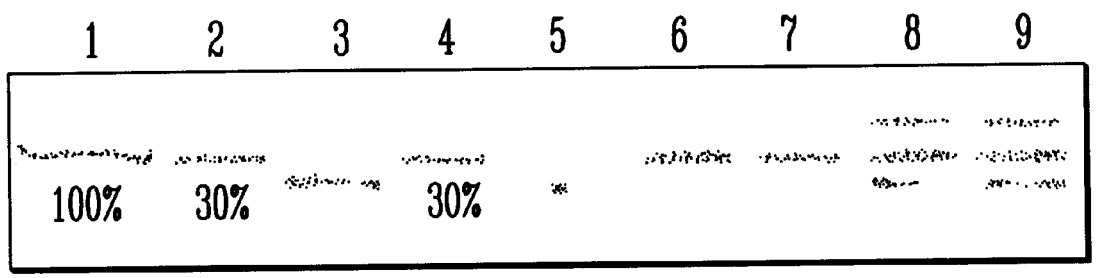
FIG. 12: is a Western blot analysis of corn kernels before and after extraction. Lanes: 1) before extraction; 2) after extraction at pH 7.5 without ME and SDS; 3) after extraction at pH 7.5 with ME and SDS; 4) after extraction at pH 10.0 without ME and SDS; 5) after extraction at pH 10.0 with ME and SDS; 6,7,8,9) 0.05, 0.01, 0.1 and 0.2 μg GUS.

To determine whether a complete extraction of rGUS from corn kernels, full-fat germ and defatted germ was achieved, the remaining solids were stained with X-Gluc. The visual examination of the spent solids revealed the presence of blue stained particles indicating an incomplete extraction of rGUS from ground corn kernels, full-fat germ, and defatted germ. The Western blot analysis of the spent solids confirmed the presence of unextracted rGUS. We estimated that about 70% of rGUS was extracted from the ground kernels with the phosphate or borate buffer alone (FIG. 12, lanes 2 and 4). Changing the pH of the extraction buffer to pH 10 did not affect the extraction efficiency. When 1% (v/v) of SDS and 2% (v/v) of ME were included in the extraction buffer rGUS was completely extracted (FIG. 12, lane 3), but the enzyme was inactive. The subsequent dialysis of SDS did not yield active protein. Interestingly, a complete extraction of rGUS could not be achieved when either SDS or ME was missing in the extraction buffer suggesting a synergistic action of these two components.

Further attempts to increase the extraction yield by adding 1% (v/v) of either Triton X-100 or Tween-20 to the extraction buffer did not show any yield improvement. Because in general, the primary product recovery is critical for effective downstream processing, an additional research effort to maximize the extraction yield of rGUS will be needed.

Distribution of rGUS in the Kernel

The fractionation of the transgenic kernels into hulls, endosperm, and germ tissue, showed that approximately 93% of the total rGUS activity was located in the germ and the remaining 7% in the endosperm (Table 8). The staining of the kernel cross-sectional area with X-Gluc solution confirmed that majority of rGUS activity was produced in the germ tissue. Neither the extraction nor the tissue staining showed any rGUS accumulation in the hulls. Because the germ usually accounts for 10–13% of the dry kernel weight and contains 93% of rGUS activity, the separation of the germ tissue before the protein extraction step could considerably reduce the cost of downstream processing by reducing the amount of total solids in the process and by increasing the concentration of rGUS in the extract. For example, the concentration of the rGUS ($\mu$g/mg of soluble protein) in the germ extract was twice as high as that in the whole kernel extract (Table 9).

Effect of the Starting Material on the Extraction and Purification of rGUS

Because the distribution study showed that more than 90% of rGUS is located in the germ, we have separated the germ by a dry-milling process. The degermination of transgenic corn kernels performed in our laboratory resulted in a germ-rich fraction of 50% purity; the balance consisted of endosperm and hulls. After extracting the corn oil from part of the germ-rich fraction, the three different starting materials (ground kernels, full-fat germ, and defatted germ) containing rGUS activity were extracted and compared (Table 9). The ground kernel, full-fat germ, and defatted germ fractions contained 3.3, 20.0, and 2.0% (w/w) corn oil, respectively (Table 9). The rGUS concentration ($\mu$g/ml) in the germ extract was six-to ten times greater than that in kernel extract at either 1:4 or 1:10 solid-to-liquid. Because total corn protein concentration was also greater in the germ than in the kernel extract, the concentration of RGUS was approximately 0.4 % and 0.2% of the total soluble protein in the germ and the kernel extract, respectively. For all three starting materials, 30% more rGUS and soluble protein per gram of dry solids were extracted at 1:10 than at 1:4 solid-to-liquid ratio. The amounts of rGUS extracted from the full-fat germ and defatted germ at either 1:4 or 1:10 solid-to-liquid ratio were similar indicating that 1) the corn oil extraction with hexane (~60° C.) did not affect the activity of rGUS, and 2) the high-oil content (20%) in the initial material did not interfere with the protein extraction. The stability of rGUS during hexane extraction is an important finding which shows that, prior to the protein extraction, the corn oil could be recovered and sold as a co-product. When full-fat germ is considered as a starting material for recovery of recombinant proteins, 1:10 solid-to-liquid ratio is recommended because at 1:4 ratio the extract was rather viscous. Although not observed on a lab-scale, the increased extract viscosity could be a problem in the scaled-up-capture chromatography step.

The purification data summarized in Table 10 indicate that rGUS can be purified with a similar effectiveness from either extract. Apparently, neither starch in the kernel extract nor the oil presence in full-fat germ extract affected the purification yield and the final purity (specific activity) of rGUS, which was estimated at 50%. To determine whether and how much the extract impurities would foul the DEAE resin after repeated use, we have performed ten on-and-off capture chromatography cycles using the full-fat germ extract (1:10 ratio). No change in the resin capacity and rGUS yield was observed after ten cycles. The rGUS concentration factor achieved after the capture chromatography step was fifteen fold for the kernel extract and five fold for the germ extracts, whereas the purification factor for all three extracts was about five fold.

TABLE 7

Conditioning schedule for germ separation from corn kernels

| Moisture content (% wet basis) | Holding time (h) |
|---|---|
| IM to 16 | 16 |
| 16 to 21 | 1.5 |
| 21 to 24 | 0.25 |

IM - initial moisture (12–14%)

TABLE 8

Distribution of rGUS in the corn kernel

|  | Germ | Endosperm |
|---|---|---|
| Amount of tissue (%) | 13 | 80 |
| rGUS activity (U/g tissue) | 6800 | 80 |
| rGUS activity (%) | 93 | 7 |

TABLE 9

Extraction of rGUS from ground corn kernels, full-fat germ, and defatted germ[a]

| Sample | Corn kernels | Full-fat germ | De-fatted germ | Corn kernels | Full-fat germ | De-fatted germ |
|---|---|---|---|---|---|---|
| Solid-to-liquid ratio | 1:4 | 1:4 | 1:4 | 1:10 | 1:10 | 1:10 |
| Initial oil content (%, db) | 3.3 | 20.0 | 2.0 | 3.3 | 20.0 | 2.0 |
| rGUS (μg/ml) | 5 | 35 | 60 | 2 | 16 | 23 |
| rGUS (μg/g dry solids) | 17 | 170 | 180 | 23 | 220 | 220 |
| rGUS (μg/mg soluble protein) | 1.9 | 3.4 | 3.9 | 1.8 | 3.6 | 3.5 |
| Total protein (mg/g dry solids) | 9.3 | 50 | 47 | 13 | 61 | 61 |

[a]All values are average of two replications with less then 10% deviation

Example 3

Cost Comparisons Using Germ

The following demonstrates the cost savings that is expected in using the germ portion of the seed for protein expression, extraction and purification, versus using the entire seed. Table 11 demonstrates production of a protein useful in pharmaceutical applications will result in production costs expected to be $\frac{1}{10}^{th}$ the cost of using the seed. In this projection, protein production is expected to be higher, since the starting material will contain a higher concentration of protein per kilogram of material versus the seed. Thus, more protein will be produced from a smaller amount of material. At 80% purification yield shown, there is a more than six times cost difference. In fact, purification yields using germ are expected to reach 85%, which would resulted in an 8 times greater cost savings in using germ. Table 12 shows details of costs to produce defatted germ containing the protein.

Yet another comparison, using rGUS purification from flake corn, full fat germ and defatted germ further demonstrates the higher yield, better purification and high quantities of rGUS per sample, summarized at Table 13. Tables 14 and 15 compare costs of extracting rGUS from full-fat corn germ and flaked corn, respectively. As can be seen there is considerable savings in using germ.

TABLE 11

Projected Cost Comparison of Protein Production Using Germ vs. Seed

| Large Scale Protein Production from Germ in Corn | Large scale Protein Production in Corn |
|---|---|
| Assumptions: | Assumptions: |
| 1. Starting material: 45,500 kg/batch flaked germ | 1. Starting material: 45,500 kg/batch flaked corn |
| 2. Defatted germ cost $2.80/kg (cost of corn + dry milling + oil extraction)-see Table 12 below | 2. Flaked corn cost: $0.16/kg (cost of corn + milling) |
| 3. Recombinant protein concentration: 1 wt % of germ | 3. Rec. protein concentration: 0.1 wt % of seed |
| 4. 45,00 kg germ contains 4500 kg of extractable corn protein and 450 kg of extractable rec. protein | 4. 45,500 kg flaked corn will contain 430 kg extractable corn protein and 45 kg of extractable rec. protein |
| 5. 10 workers/shift operating in 3 shifts | 5. 10 workers/shift operating in 3 shifts |
| 6. Final protein product will contain 20 wt % recombinant protein | 6. Final protein product will contain 20 wt. % recombinant protein |
| 7. Purification yield - 80% | 7. Purification yield - 80% |
| 8. Credits: | 8. Credits: |
|  | • hominy feed @$0.10/kg |

TABLE 11-continued

Projected Cost Comparison of Protein Production Using Germ vs. Seed

| Large Scale Protein Production from Germ in Corn | | Large scale Protein Production in Corn | |
|---|---|---|---|
| • grits @$0.33/kg | | | |
| • crude oil @$0.52/kg | | | |
| • hominy fee @$0.10/kg | | | |
| Simulation Results: | | Simulation Results: | |
| Total Equipment cost: | $3,800,000 | Total Equipment Cost: | $3,520,000 |
| Direct Fixed Capital: | $24,000,000 | Direct Fixed Capital: | $22,000,000 |
| Total Annual Operating Cost: | $70,000,000 | Total Annual Operating Cost: | $16,600,000 |
| Total Credits: | $46,000,000 | Credits: | $1,600,000 |
| Grits Credits | $41,000,000 | | |
| Grits Credits | $41,000,000 | | |
| Crude oil | $1,800,000 | | |
| Feed | $3,200,000 | | |
| Rec. Protein (kg/yr) | 150,000 | Protein Product (kg/yr): | 15,000 |
| Rec. Protein Production Cost ($/kg): | $160 | Rec. Production Cost ($/kg): | $1,130 |

TABLE 12

Cost to Produce Defatted Germ Containing HSA

| | Amount (kg) | Total Cost ($) | Unit Cost ($kg) | Comments |
|---|---|---|---|---|
| Raw Material | 45,000 | 7,200 | 0.16 | $0.16/kg |
| Transgenic Corn | | | | |
| Processing | | | | |
| Dry-milling | 45,000 | 1,800 | 0.04 | $0.04/kg ($1/bu) |
| Germ-oil extraction | 3,150 | 126 | 0.04 | 10% germ, 70% germ yield: Extr. Cost = $0.04/kg germ flakes |
| Total Cost | | 9,126 | | |
| Co-Product Credits | | | | |
| Grits | 22,500 | 7425 | 0.33 | Assume 50% of total corn |
| Crude oil | 598.5 | 311.22 | 0.52 | 20% oil content |
| Hulls + tip caps (7% of corn) | 3,150 | 693 | | |
| Hominy feed (Hulls + tip caps + germ) | 6,300 | | 0.11 | |
| Total Credits | | 8429 | | |
| NET PRODUCTION COST of 1 kg germ | 3150 | 697 | 0.22 | |
| Unit Cost of HSA before recovery and purification | 31.5 | | 22 | HSA content 0.1 wt % of corn or 1 wt % of germ |

TABLE 13

Comparison of rGUS Purification from Different Samples

| Sample | Flaked corn | Full-fat germ | Defatted germ |
|---|---|---|---|
| Solid-to-liquid ratio | 1:4 | 1:10 | 1:10 |
| Yield (%) | 36 | 44 | 47 |
| Purification fold | 300 | 350 | 330 |
| Specific activity, (U/mg) | 36,000 | 45,000 | 36,000 |
| Purified rGUS per g sample, (mg/g) | 0.006 | 0.040 | 0.056 |

TABLE 14

Cost of Extracting rGUS from Full-fat Corn Germ

| Processing Cost | $/day | $/kg corn | $/lb corn | $/bu corn |
|---|---|---|---|---|
| Germ separation | 681.75 | 0.150 | 0.068 | 3.82 |
| Extraction | 54.70 | 0.012 | 0.005 | 11.20 |
| Drying | 14.61 | 0.003 | 0.001 | 0.08 |
| TOTAL | 751.06 | 0.165 | 0.075 | 15.10 |
| Cost of Materials | | | | |
| Corn | 2,000 | 0.440 | 0.200 | 11.20 |
| Water | 0.21 | 0.000 | 0.000 | 0.00 |
| Na2HPO4 | 34.11 | 0.008 | 0.003 | 0.19 |
| NaH2PO4 | 4.41 | 0.001 | 0.000 | 0.02 |
| TOTAL | 2,038.74 | 0.449 | 0.204 | 11.42 |

TABLE 14-continued

Cost of Extracting rGUS from Full-fat Corn Germ

| Processing Cost | $/day | $/kg corn | $/lb corn | $/bu corn |
|---|---|---|---|---|
| Co-product Credits | | | | |
| Dry spent solids | 474.64 | 0.104 | 0.005 | 0.27 |
| TOTAL | 474.64 | 0.104 | 0.005 | 0.27 |
| TOTAL COST | 2,315.15 | 0.509 | 0.274 | 26.25 |
| rGUS in extract (kg) | 0.067 | 0.134 | 0.201 | |
| Cost/kg rGUS | $34,523 | $17,261 | $11,508 | |

TABLE 15

Cost of Extracting rGUS from Flaked Corn

| Processing Cost | $/day | $/kg corn | $/lb corn | $/bu corn |
|---|---|---|---|---|
| Milling | 92.71 | 0.020 | 0.009 | 0.52 |
| Extraction | 710.23 | 0.156 | 0.071 | 3.98 |
| Drying | 340.13 | 0.075 | 0.034 | 1.90 |
| TOTAL Cost of Materials | 1,143.07 | 0.251 | 0.114 | 6.40 |
| Corn | 2,000 | 0.440 | 0.200 | 11.20 |
| Water | 2.73 | 0.001 | 0.000 | 0.02 |
| Na2HPO4 | 443.06 | 0.097 | 0.044 | 2.48 |
| NaH2PO4 | 57.33 | 0.013 | 0.006 | 0.32 |
| TOTAL Co-product Credits | 2,503.11 | 0.551 | 0.250 | 14.02 |
| Dry spent solids | 441.52 | 0.097 | 0.044 | 2.47 |
| TOTAL | 441.52 | 0.097 | 0.044 | 2.47 |
| TOTAL COST | 3,204.66 | 0.705 | 0.320 | 17.95 |
| rGUS in extract (kg) | 0.089 | 0.177 | 0.266 | |
| Cost/kg extractable GUS | $36,209.14 | $18,104.57 | $12,069.71 | |

REFERENCES

1. Benfey P N, Chua N-H: Regulated genes in transgenic plants. Science 244:174–181 (1989).
2. Fisk H J, Dandekar A M: The introduction and expression of transgenes in plants. Scientia Hort. 55:5–36 (1993). 3. Pen J, Sijmons P C, van Ooijen A J J, Hoekema A: Protein production in transgenic crops: Analysis of plant molecular farming. Industrial Crops Production. Elsevier, Amsterdam. pp. 241–250 (1993B).
4. Callis J, Fromm M, Walbot V: Introns increase gene expression in cultured maize cells. Genes and Development 1: 1183–1200 (1987).
5. Christensen A M, Sharrock R A, Quail P H: Maize polyubiquitin genes: structure, thermal perturbation of expression and transcript splicing, and promoter activity following transfer to protoplasts by electroporation. Plant Mol. Biol. 18:675–689 (1992).
6. Comejo M, Luth D, Blankenship K, Anderson, Blechl A: Activity of a maize ubiquitin promoter in transgenic rice. Plant Mol. Biol. 23: 567–581 (1993).
7. An G, Mitra A, Choi H K, Costa M A, An K, Thornburg R W, Ryan C A:. Runctional analysis of the 3' control region of the potato wound-inducible proteinase inhibitor II gene. Plant Cell 1: 115–122 (1989).
8. Jones R L, Robinson D G: Protein secretion in plants. New-Phytol. New York, N.Y.: Cambridge University Press. April 1989. v. 111 (4) p. 567–597. ill.
9. Staehelin L A, Moore I: The plant golgi apparatus: Structure, functional organization and trafficking mechanisms. Ann. Rev. Plant Physiol. Plant Mol. Biol. 46:261–288 (1995).
10. van der Hoeven C., Dietz A., Landsmann J: Variability of organ-specific gene expression in transgenic tobacco plants. Transgenic Res. 3:159–166 (1944)
11. DeLange R J, Huang T S: Egg White Avidin III. Sequence of the 75-residue middle cyanogen bromide peptide. Complete amino acid sequence of the protein subunit. J. Biol. Chem. 246: 698–709 (1971).
12. Gope M L, Keinanen R A, Kristo P A, Conneely O M, Beattie W G, Zarucki-Schulz T, O'Malley B W, Kulomaa M S: Molecular cloning of the chicken avidin cDNA. Nuc. Acids Res. 15: 3595–3606 (1987).
13. Keinanen R A, Laukkanen M-L, Kulomaa M S: Molecular cloning of three structurally related genes for chicken avidin. J. Steroid Biochem. 30: 17–21 (1988).
14. Keinanen R A, Wallen M J, Kristo P A, Laukkanen M O, Toimela T A, Helenius M A, Kulomaa M S: Molecular cloning and nucleotide sequence of chicken avidin-related genes 1–5. Eur. J. Biochem. 220: 615–21 (1994).
15. Rogers J C: Two barley alpha-amylase gene families are regulated differently in aleurone cells. J. Biol. Chem. 260:3731–3738 (1985).
16. Nagy F, Odell J T, Morelli G, Chua N H: Properties of expression of the 35S promoter from CaMV in transgenic tobacco plants. Biotechnology in plant science: relevance to agriculture in the eighties. Milton Zaitlin, Peter Day, and Alexander Hollaender, eds. Academic Press, Orlando, Fla. p. 227–235 (1985).
17. Gallie D R, Sleat D E, Watts J W, Turner P C, Wilson T M A: The 5'-leader sequence of tobacco mosaic virus RNA enhances the expression of foreign gene transcripts in vitro and in vivo. Nuc. Acids Res. 15:3257–3273 (1987).
18. Armstrong C L, Green C E, Phillips R L: Develpment and availability of germplasm with high Type II culture formation response. Maize Gen. Coop. Newsletter, 65:92–93 (1991). Bradford M: A rapid and sensitive method for the quantification of microgram quantities of protein utilizing the principle of protein-dye binding. Anal. Biochem. 72:248–254 (1976).
19. Tomes D T, Ross M C, Songstad D D: Direct DNA transfer into intact plant cells via microprojectile bombardment. O L Gamborg and G C Phillips, eds., Plant Cell Tissue and Organ Culture: Fundamental Methods. Springer-Verlag, Berlin, Heidelberg. pp.197–213 (1995).
20. Hancock K, Tsang VCW: India ink staining of protein on nitrocellulose paper. Anal. Biochem. 133:157–162 (1983).
21. Fritz S E, Hood K R, Hood E E: Localization of soluble and insoluble fractions of hydroxyproline-rich glycoproteins during maize
22. Rogers S O, Bendich A J: Extraction of DNA from milligram amounts of fresh, herbarium and mummified plant tissues. Plant Mol. Biol. 5:69–73 (1985).
23. Lowe K, Bowen B, Hoerster G, Ross M, Bond D, Pierce D, Gordon-Kamm B: Germiline transformation of maize following manipulation of chimeric shoot meristems. Bio/Technology 13:677–682 (1995).
24. Jhingan A K: A novel technology for DNA isolation. Methods Mol. Cell. Biol. 3:15–22 (1992).

25. Bradford M: A rapid and sensitive method for the quantification of microgram quantities of protein utilizing the principle of protein-dye binding. Anal. Biochem. 72:248–254 (1976).
26. Laemmli U K: Cleavage of structural proteins during the assembly of the head of the bacteriophage T4. Nature 227:680–685 (1970).
27. Witcher D R, DeWaard M, Liu H, Pragnell M, Campbell K P: Association of native $Ca^{2+}$ channel B subunits with the al subunit interaction domain. J. Biol. Chem. 270:18088–18093 (1995). 28. Sharp A H, Campbell K P: Characterization of the 1,4-dihydropyridine receptor using subunit-specific polyclonal antibodies: evidence for a 32,000 Da subunit. J. Biol. Chem. 264:2816–2825 (1989).
29. Green N M: Spectrophotometric determination of avidin and biotin. Meth. Enzym. 118A:418–422 (1970).
30. Durance T. D: Residual avidin activity in cooked egg white assayed with improved sensitivity. J. Food Sci. 56:707 (1991).
31. Bjerrum O J, Schafer-Nielsen C: Analytical electrophoresis, Dunn, M. J. (ed.) Verlag Chemie, Weinheim, p.315 (1986)
32. Heney G, Orr G A: The purification of avidin and its derivatives on 2-iminobiotin-6-aminohexyl-sepharose 4B. Anal. Biochem. 114:92–96 (1981).
33. Gordon-Kamm W J, Spencer T M, Mangano M L, Adams T R, Daines R J, Start W G, O'Brian J V, Chambers S A, Adams Jr. W R, Willetts N G, Rice T B, Mackey C J, Krueger R W, Kausch A P, Lemaux P G: Transformation of maize cells and regeneration of fertile transgenic plants. Plant Cell 2:603–618 (1990). 34. Matsudaira P: Sequence from picomole quantities of proteins electroblotted onto polyvinylidene difluoride membranes. J. Biol. Chem. 262:10035–10038 (1987)
35. Hiller Y, Gershoni J M, Bayer E A, Wilchek M: Biotin binding to avidin. Biochem J. 248:167–171 (1987).
36. Hood, E. E.; Maddock, S.; Meyer, T.; Baszczynski, C.; Register, J.; Marshall, L.; Bond, D. Kullisek, E.; Howard, J. A. Commercial Production of Avidin from Transgenic maize: I. Plant Transcription Unit, Transformation, and Characterization of Transformant. Molecular Breeding. 1996a. Submitted.
37. Jefferson, R. A.; Wilson, K. J. (1991). In The GUS Gene Fusion system. In "Plant Molecular Biology Manual", Vol. 1, B14, (S. B. Gelven, R. A. Schilperoort and D. P. S. Verma, eds.). Kluwer Academic Publisher, Dordrecht, Belgium. pp. 1–33.
38. Bradford, M. A rapid and Sensitive Method for the Quantitation of Microgram Quantities of Protein Utilizing the Principle of Protein-dye Binding. Anal. Biochem. 1976, 72,248–254.
39. Laemmli U. K. Cleavage of Structural Proteins During the Assembly of the Head of the Bacteriophage T4. Nature. 1970, 227, 680–685.

What is claimed is:

1. A method of commercial production of a heterologous protein in plant germ comprising:
(a) transforming monocotyledonous plant tissue with a nucleotide sequence expressing the protein linked to a ubiquitin promoter;
(b) culturing a plant from the plant tissue;
(c) growing the plant such that it produces seed having germ and harvesting the seed;
(d) separating the germ from the seed such that the germ has increased concentration of protein on a dry weight basis.

2. A method of decreasing the amount of plant tissue necessary to supply commercial quantities of heterologous protein produced in the plant, wherein the method comprises transforming monocotyledonous plant tissue with a nucleotide sequence encoding the protein linked to a ubiquitin promoter, growing a plant from the tissue such that it produces seed, separating the germ tissue from the seed and supplying the germ tissue as a source of commemial quantities of the protein.

3. A method of supplying heterologous protein produced in plants in a pharmaceutical, veterinary, agriculture or industrial use, wherein the method comprises transforming monocotyledonous plant tissue with a nucleotide sequence encoding the protein linked to a ubiqituin promoter, growing a plant from the plant tissue such that the plant produces seed having germ, separating the germ from the seed and supplying the germ as the source of the heterologous protein for said use.

4. A method of supplying heterologous protein expressed in plants for commercial applications, wherein the method comprises transforming monocotyledonous plant tissue with a nucleotide sequence encoding the protein linked to a ubiqutin promoter, growing a plant from the tissue such that it produces seed having germ, separating the germ tissue from the seed of the plant and supplying the germ tissue as the source of the protein in commercial applications.

5. A method of improving recovery of costs of production of heterologous protein in plants, wherein the method comprises transforming monocotyledonous plant tissue with a nucleotide sequence encoding the protein linked to a ubiquitin promoter, growing a plant from the tissue such that it produces seed having germ, separating the gean tissue from the seed, supplying the germ tissue to a commercial application and supplying the remaining tissue of the seed to a second commercial application.

* * * * *